US011669960B2

(12) United States Patent
Ichinose et al.

(10) Patent No.: US 11,669,960 B2
(45) Date of Patent: Jun. 6, 2023

(54) LEARNING SYSTEM, METHOD, AND PROGRAM

(71) Applicant: FUJIFILM Corporation, Tokyo (JP)

(72) Inventors: Akimichi Ichinose, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/927,956

(22) Filed: Jul. 13, 2020

(65) Prior Publication Data

US 2020/0342257 A1  Oct. 29, 2020

Related U.S. Application Data

(63) Continuation of application No. PCT/JP2018/047854, filed on Dec. 26, 2018.

(30) Foreign Application Priority Data

Jan. 24, 2018  (JP) .............................. JP2018-010015

(51) Int. Cl.
*G06T 5/50* (2006.01)
*G06F 18/22* (2023.01)
(Continued)

(52) U.S. Cl.
CPC .......... *G06T 7/0012* (2013.01); *G06F 18/214* (2023.01); *G06F 18/22* (2023.01);
(Continued)

(58) Field of Classification Search
CPC ............... G06K 9/6214; G06K 9/6215; G06K 9/6255; G06K 9/6256; G06T 5/50;
(Continued)

(56) References Cited

U.S. PATENT DOCUMENTS 6,480,627 B1    11/2002  Mathias et al.
10,977,580 B1*   4/2021  Florez Choque ........ G06N 3/08
(Continued)

FOREIGN PATENT DOCUMENTS

JP    2003503801    1/2003
JP    2009240464    10/2009
(Continued)

OTHER PUBLICATIONS

G. Wang, C. X. Dang and Z. Zhou, "Measure Contribution of Participants in Federated Learning," 2019 IEEE International Conference on Big Data (Big Data), 2019, pp. 2597-2604, doi: 10.1109/BigData47090.2019.9006179. (Year: 2019).*
(Continued)

*Primary Examiner* — Sean M Conner
*Assistant Examiner* — Stephen M Brinich
(74) *Attorney, Agent, or Firm* — JCIPRNET

(57) ABSTRACT

Provided are a learning system, a method, and a program that can provide medical institutions with motivation for creating learning data related to medical images in a case of using machine learning to support diagnosis using medical images. The learning system includes a reception unit that receives an input of first learning data from a user, a calculation unit that calculates, a contribution degree of the first learning data to learning of a discriminator for each user on the basis of at least one of a comparison result between the first learning data and second learning data used for creating the discriminator or a comparison result between an output obtained by inputting the first learning data to the discriminator and correct answer data corresponding to the first learning data, and a service setting unit that sets a service for the user on the basis of the contribution degree calculated for each user.

9 Claims, 18 Drawing Sheets

(51) Int. Cl.
  *G06V 10/772* (2022.01)
  *G06T 7/00* (2017.01)
  *G06F 18/214* (2023.01)
  *G06V 10/774* (2022.01)
  *G06V 10/776* (2022.01)
  *G06V 10/82* (2022.01)

(52) U.S. Cl.
  CPC .............. *G06T 5/50* (2013.01); *G06V 10/772* (2022.01); *G06V 10/774* (2022.01); *G06V 10/776* (2022.01); *G06V 10/82* (2022.01); *G06T 2207/20081* (2013.01)

(58) Field of Classification Search
  CPC ...................... G06T 7/00; G06T 7/0002; G06T 2207/20081; G06T 2207/20084; G06N 20/00; G06N 20/20
  USPC ....................... 382/155–159, 100; 700/47–48
  See application file for complete search history.

(56) References Cited

U.S. PATENT DOCUMENTS

| | | | |
|---|---|---|---|
| 11,004,022 B1* | 5/2021 | Ghalaty | ......... G06Q 10/063118 |
| 2011/0026800 A1 | 2/2011 | Tonomura et al. | |
| 2014/0206997 A1 | 7/2014 | Tonomura et al. | |
| 2016/0274779 A9* | 9/2016 | Rosenberg | .............. H04L 67/12 |
| 2017/0124655 A1* | 5/2017 | Crabtree | ................ G06Q 40/04 |
| 2019/0172493 A1* | 6/2019 | Khan | ................... G11B 27/102 |
| 2019/0354896 A1* | 11/2019 | Kobayashi | ............. G06N 20/00 |
| 2020/0057958 A1* | 2/2020 | Moore | .................... G06F 16/90 |
| 2021/0042645 A1* | 2/2021 | Sharma | ............... G06F 16/2379 |
| 2021/0158099 A1* | 5/2021 | Tuor | .................... G06K 9/6267 |

FOREIGN PATENT DOCUMENTS

| | | |
|---|---|---|
| JP | 2016168046 | 9/2016 |
| JP | 2017067489 | 4/2017 |
| WO | 2012165529 | 12/2012 |

OTHER PUBLICATIONS

T. Scmitsu, M. Nakamura, S. Ishigami, T. Aoki, T-y. Lee and Y. Isu, "Estimating Contribution of Training Datasets using Shapley Values in Data-scale for Visual Recognition," 2021 17th Int'l Conf. on Machine Vision and Applications (MVA), 2021, pp. 1-5, doi: 10.23919/MVA51890.2021.9511396. (Year: 2021).*

"International Search Report (Form PCT/ISA/210)" of PCT/JP2018/ 047854, dated Mar. 12, 2019, with English translation thereof, pp. 1-4.

"Written Opinion of the International Searching Authority (Form PCT/ISA/237)" of PCT/JP2018/047854, dated Mar. 12, 2019, with English translation thereof, pp. 1-7.

* cited by examiner

LEARNING SYSTEM, METHOD, AND PROGRAM

CROSS-REFERENCE TO RELATED APPLICATIONS

The present application is a Continuation of PCT International Application No. PCT/JP2018/047854 filed on Dec. 26, 2018 claiming priority under 35 U.S.C § 119(a) to Japanese Patent Application No. 2018-010015 filed on Jan. 24, 2018. Each of the above applications is hereby expressly incorporated by reference, in its entirety, into the present application.

BACKGROUND OF THE INVENTION

1. Field of the Invention

The present invention relates to a learning system, a method, and a program, and particularly, to a learning system, a method, and a program that performs learning for supporting diagnosis using medical images.

2. Description of the Related Art

In medical institutions, a patient may be diagnosed using medical images. In the diagnosis using medical images, an examination part of the patient is imaged, and a physician interprets medical images of the examination part to diagnose whether or not there is a lesion in the examination part.

It has been proposed to use machine learning (including deep learning and artificial intelligence (AI)) to support a physician in making a diagnosis using medical images.

As a system for performing learning for classifying images, JP2003-503801A discloses an image classification system including a learning system. The image classification system disclosed in JP2003-503801A comprises a classifier that determines the classification of the image, and a performance evaluator. The performance evaluator compares the classification obtained as the result of the image classification with a correct image classification. In the image classification system disclosed in JP2003-503801A, accuracy of the image classification system can be measured on the basis of the coincidence between the classification obtained as the result and the correct classification.

SUMMARY OF THE INVENTION

In general, organs (for example, bones, organs, lesions, or the like) included in medical images vary in shape, size, and type. Therefore, in a case where using machine learning to support a diagnosis using the medical images, in order to improve the accuracy of finding and diagnosing a lesion, it is necessary to collect and learn medical images having various shapes and sizes for each type of organ.

In a case where an individual medical institution accumulates medical images acquired from patients, the medical image acquisition source is limited to patients at each medical institution. For this reason, it is difficult for each medical institution to collect the medical images of various shapes and sizes for each type of organ. Therefore, in order to collect various medical images, it is conceivable that a plurality of medical institutions collect medical images in cooperation, and use the collected medical images to perform learning of a medical image identification engine.

However, in a case of performing the learning by collecting the medical images, it is necessary to provide correct answer data to learning data including the medical images. Such correct answer data is provided by a physician who is in charge of interpreting the medical images. In a case where using machine learning to support diagnosis using medical images, it is preferable to improve the accuracy of the medical image identification engine by making it possible to continuously collect learning data to which the correct answer data has been provided from a plurality of medical institutions.

However, in a case where one medical image includes a plurality of lesions or the size of the lesion is small, even a professional physician may have difficulty finding the lesion included in the medical image without error. In addition, regarding a lesion having relatively few past cases (for example, a rare disease or a rare case that is not a rare disease), even a professional physician may have difficulty finding and diagnosing the lesion.

In this way, performing the interpretation of medical images to create learning data is an operation that is burdensome and takes a lot of time, even for an experienced professional physician. For this reason, continuous creation of learning data for the learning of the medical image identification engine imposes a heavy burden on medical institutions and physicians. As a result, it has been difficult to maintain motivation for the medical institutions and the physicians to create the learning data.

The present invention has been made in view of such circumstances, and an object of the invention is to provide a learning system, a method, and a program that can provide medical institutions with motivation for creating learning data related to medical images in a case of using machine learning to support diagnosis using medical images.

In order to solve the above problems, a learning system according to a first aspect of the present invention comprises a reception unit that receives an input of first learning data from a user, a calculation unit that calculates, a contribution degree of the first learning data to learning of a discriminator for each user on the basis of at least one of a comparison result between the first learning data and second learning data used for creating the discriminator or a comparison result between an output obtained by inputting the first learning data to the discriminator and correct answer data corresponding to the first learning data, and a service setting unit that sets service for the user on the basis of the contribution degree calculated for each user.

According to the first aspect, in addition to collecting learning data including medical images from a plurality of medical institutions and causing the medical image identification engine to perform learning, a service for the medical institutions can be set in consideration of the contribution degree of the medical image identification engine to learning. As a result, the medical institution can be motivated to create learning data, so that it is possible to continuously collect the medical images from the plurality of medical institutions and improve the accuracy of the medical image identification engine.

The learning system according to a second aspect of the present invention is, in the first aspect, a system in which the calculation unit calculates the contribution degree on the basis of a difference between a comparison data set including the second learning data used for creating the discriminator and the first learning data.

The learning system according to a third aspect of the present invention is, in the second aspect, a system in which the calculation unit calculates the contribution degree on the basis of a difference between a feature vector obtained from an image included in the second learning data and a feature vector obtained from an image included in the first learning data.

The learning system according to a fourth aspect of the present invention is, in the first aspect, a system in which the calculation unit calculates the contribution degree on the basis of a difference between average data created from the second learning data used for creating the discriminator and the first learning data.

The learning system according to a fifth aspect of the present invention is, in the fourth aspect, a system in which the calculation unit calculates the contribution degree on the basis of a difference between a feature vector obtained from an average image created from the image included in the second learning data and a feature vector obtained from an image included in the first learning data.

According to the second to fifth aspects, a magnitude of a difference between the first learning data and the second learning data can be reflected in the contribution degree.

The learning system according to a sixth aspect of the present invention further comprises, in the any one of the first to fifth aspects, an input unit that receives an input of the correct answer data for an output obtained by inputting the first learning data to the discriminator, in which the calculation unit calculates the contribution degree on the basis of a result of comparing the output with the correct answer data.

The learning system according to a seventh aspect of the present invention is, in the sixth aspect, a system in which the input unit receives an input of correction of at least one of a contour or a size of a region extracted from an image included in the first learning data by the discriminator, and the calculation unit calculates the contribution degree on the basis of an amount of the correction.

According to the sixth and seventh aspects, the result of correction for the output of the discriminator can be reflected in the contribution degree.

The learning system according to an eighth aspect of the present invention is, in the any one of the first to seventh aspects, a system in which the calculation unit calculates a difference in accuracy of an image analysis result in the discriminator before and after learning using the first learning data, and calculates the contribution degree of the first learning data to learning of the discriminator for each user on the basis of the difference in accuracy.

The learning system according to a ninth aspect of the present invention is, in the any one of the first to eighth aspects, a system in which the reception unit receives an input of data including a medical image of a patient as the first learning data, and the learning system further comprises a data processing unit that creates and stores data in which identification information capable of identifying the patient is concealed, in the first learning data.

A learning method according to a tenth aspect of the present invention comprises, in a learning system, a step of receiving an input of first learning data from a user, a step of calculating a contribution degree of the first learning data to learning of a discriminator for each user on the basis of at least one of a comparison result between the first learning data and second learning data used for creating the discriminator or a comparison result between an output obtained by inputting the first learning data to the discriminator and correct answer data corresponding to the first learning data, and a step of setting a service for the user on the basis of the contribution degree calculated for each user.

A learning program according to an eleventh aspect of the present invention causes a computer to realize a function of receiving an input of first learning data from a user, a function of calculating a contribution degree of the first learning data to learning of a discriminator for each user on the basis of at least one of a comparison result between the first learning data and second learning data used for creating the discriminator or a comparison result between an output obtained by inputting the first learning data to the discriminator and correct answer data corresponding to the first learning data, and a function of setting a service for the user on the basis of the contribution degree calculated for each user.

According to the present invention, in addition to collecting learning data including medical images from a plurality of medical institutions and causing the medical image identification engine to perform learning, a service for the medical institutions can be set in consideration of the contribution degree of the medical image identification engine to learning. As a result, the medical institution can be motivated to create learning data, so that it is possible to continuously collect the medical images from the plurality of medical institutions and improve the accuracy of the medical image identification engine.

DESCRIPTION OF THE PREFERRED EMBODIMENTS

Hereinafter, embodiments of a medical image processing apparatus, method, and program, and a diagnosis support apparatus, method, and program according to the embodiment of the present invention will be described with reference to the accompanying drawings.

First Embodiment (Medical Support System)

Figure 1:
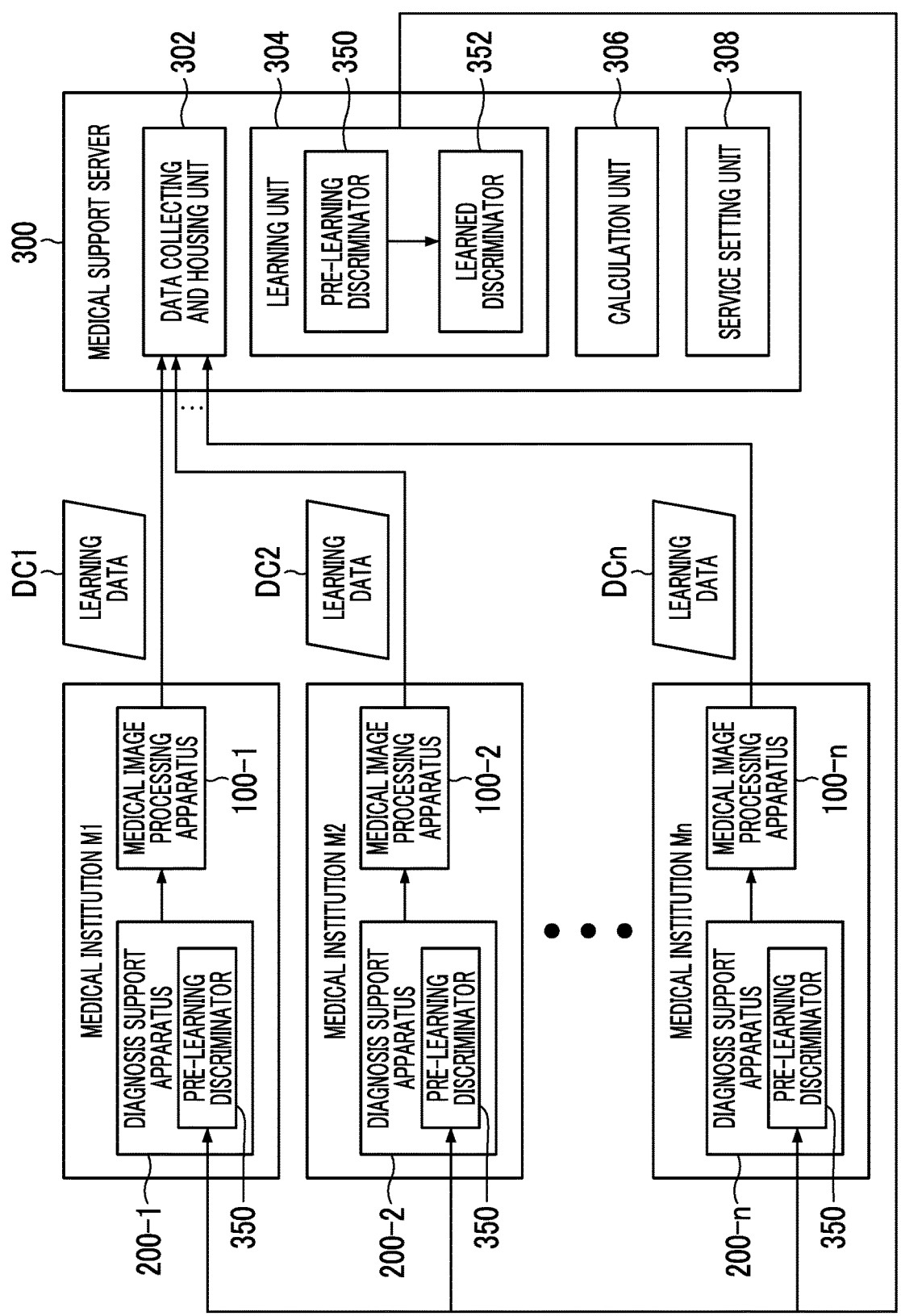
FIG. 1 is a block diagram illustrating a medical support system according to a first embodiment of the present invention.

First, an outline of the medical support system will be described with reference to FIG. 1. FIG. 1 is a block diagram illustrating a medical support system according to a first embodiment of the present invention.

As illustrated in FIG. 1, a medical support system (learning system) 10 according to the present embodiment includes medical image processing apparatus 100-1, 100-2, . . . , 100-n, diagnosis support apparatus 200-1, 200-2, . . . , 200-n, and a medical support server 300 respectively installed in the medical institutions M1, M2, . . . , Mn. The medical support server 300 includes a data collecting and housing unit 302 and a learning unit 304.

Medical institutions M1, M2, . . . , Mn are facilities that provide medical care to patients, and are, for example, hospitals, dental clinics, clinics, and the like. The medical institutions M1, M2, . . . , Mn correspond to users of a medical support system 10 according to the present embodiment.

The medical image processing apparatus 100-1, 100-2, . . . , 100-n, and the diagnosis support apparatus 200-1, 200-2, . . . , 200-n respectively installed in the medical institutions M1, M2, . . . , Mn can communicate with the medical support server 300 via a network (for example, internet or intranet). Here, the medical image processing apparatus 100-1, 100-2, . . . , 100-n, and the diagnosis support apparatus 200-1, 200-2, . . . , 200-n, and the medical support server 300 may be connected via a virtual private network (VPN), and can use an internet VPN using internet, or an internet protocol-VPN (IP-VPN) using a communication network (closed network) that is not open to the outside of an internet service provider, for example. In addition, the medical image processing apparatus 100-1, 100-2, . . . , 100-n, and the diagnosis support apparatus 200-1, 200-2, . . . , 200-n, and the medical support server 300 may be connected via a dedicated line.

The medical support server 300 may be installed in a place different from the medical institutions M1, M2, . . . , Mn (for example, a provider of a medical support service using the medical support server 300), or may be installed in one medical institution of the medical institutions M1, M2, . . . , Mn.

In the following description, the medical image processing apparatus 100-1, 100-2, . . . 100-n of the medical institutions M1, M2, . . . , Mn, and the diagnosis support apparatus 200-1, 200-2, . . . , 200-n may be abbreviated as a medical image processing apparatus 100-i and a diagnosis support apparatus 200-i (i=1, 2, . . . , n) of a medical institution Mi.

(Learning and Updating of Medical Image Identification Engine)

In the medical support system 10 according to the present embodiment, each of diagnosis support apparatus 200-i includes a medical image identification engine (a pre-learning discriminator 350) for analyzing medical images.

In the following description, the medical image identification engine before learning using learning data (first learning data) DCi collected from the medical institution Mi is referred to as the pre-learning discriminator 350, and the medical image identification engine after learning using the learning data DCi is referred to as a learned discriminator 352.

The pre-learning discriminator 350 is a medical image identification engine that has been previously learned in the medical support server 300 and provided to the diagnosis support apparatus 200-i. A learning data used for learning of the pre-learning discriminator 350 is referred to as second learning data. The learning data (first learning data) DCi and the second learning data are data including at least a medical image and analysis result information of the medical image (correct answer data), and used for supervised learning in the medical image identification engine. The supervised learning will be described later.

The diagnosis support apparatus 200-i acquires a medical image (for example, an X-ray image) and patient information (for example, patient identification information, patient identification (ID), patient name, and the like) from an examination apparatus (reference numeral 150 in FIG. 2) installed in the medical institution Mi, and analyzes the medical image using the pre-learning discriminator 350. The diagnosis support apparatus 200-i presents the diagnosis support information including the analysis result and the medical image to a physician, and receives an input such as approval or correction from the physician. Analysis result information including an analysis result in which approval or correction has been input by the physician is transmitted to the medical image processing apparatus 100-i together with the medical image and the patient information.

The medical image processing apparatus 100-i performs concealment processing for concealing identification information that can identify a patient for the data in which approval or correction has been input by the physician among the medical image, the patient information and the analysis result information to generate the learning data DCi.

The medical support server 300 collects learning data DC1, DC2, . . . , DCn respectively from the medical image processing apparatus 100-1, 100-2, . . . , 100-n of the medical institutions M1, M2, . . . , Mn by the data collecting and housing unit 302.

The data collecting and housing unit 302 comprises a storage device for housing the learning data DC1, DC2, . . . , DCn. As the storage device, for example, an apparatus including a magnetic disk such as a hard disk drive (HDD), an apparatus including a flash memory such as an embedded multi media card (eMMC), a solid state drive (SSD), or the like can be used.

The learning unit 304 of the medical support server 300 includes the pre-learning discriminator 350 that is the medical image identification engine of the same version as the medical institution Mi. The learning unit 304 causes the pre-learning discriminator 350 to perform learning using the learning data DC1, DC2, . . . , DCn collected from the medical institutions M1, M2, . . . , Mn. The learned discriminator 352 generated by the learning is transmitted respectively from the medical support server 300 to the diagnosis support apparatus 200-*i*. Thereby, the diagnosis support apparatus 200-*i* and the medical image identification engine of the medical support server 300 are updated from the pre-learning discriminator 350 to the learned discriminator 352.

The learning data DCi used for the learning in the learning unit 304 of the medical image identification engine and used for generating the learned discriminator 352 that is the updated version of the medical image identification engine is incorporated in the second learning data and held in the data collecting and housing unit 302. That is, the learning data (current the first learning data) DCi is used as the second learning data the next time the first learning data is collected and learned.

The diagnosis support apparatus 200-1, 200-2, . . . , 200-*n* of the medical institutions M1, M2, . . . , Mn updates the medical image identification engine by acquiring the learned discriminator 352 from the medical support server 300 and replacing it with the pre-learning discriminator 350, respectively. Thus, the diagnosis support apparatus 200-1, 200-2, . . . 200-*n* can analyze another medical image using the learned discriminator 352, generate the diagnosis support information including the analysis result, and present it to the physician.

(Service Setting Based on Contribution Degree)

In the medical support server 300, the learning data DCi collected from the medical institution Mi is evaluated in parallel with the learning in the learning unit 304 or before and after the learning is performed. Then, on the basis of the result of the evaluation of the learning data DCi, the service content provided to each medical institution Mi from the provider of the medical support service using the medical support server 300 is set.

A calculation unit 306 is a calculation apparatus that evaluates the learning data DCi and calculates the contribution degree for each medical institution Mi that is a user of the medical support service according to the present embodiment. A specific example of calculating the contribution degree will be described later.

A service setting unit 308 is a calculation apparatus that sets service to be provided to each medical institution Mi on the basis of the contribution degree calculated for each medical institution Mi. The service setting unit 308 can give preferential treatment in the medical support service as the contribution degree of each medical institution Mi is higher or ranking of the contribution degree is higher. For example, the service setting unit 308 may provide a point that can be used as a price for a service (including services other than medical support services (for example, provision of hardware or applications)) provided by the provider of the medical support service that increases the discount rate of the medical support service fee according to the contribution degree of each medical institution Mi.

According to the present embodiment, in addition to collecting the learning data DCi including medical images from the medical institution Mi and causing the medical image identification engine to perform learning, a service for the medical institution Mi can be set in consideration of contribution degree of the medical image identification engine to learning. As a result, the medical institution Mi can be motivated to create learning data, so that it is possible to continuously collect the medical images from the plurality of medical institutions Mi and improve the accuracy of the medical image identification engine.

The learning in the learning unit 304 and the update of the medical image identification engine may be performed periodically. In addition, the learning in the learning unit 304 and the update of the medical image identification engine may be performed according to the capacity of the learning data DCi transmitted to and accumulated in the medical support server 300, for example, in a case where the number of accumulated medical images becomes equal to or more than a predetermined number. In addition, the execution timing of the learning in the learning unit 304 and the update of the medical image identification engine may be randomly set by an operator. Further, in a case where it is determined that the importance is high according to the importance of the correction of the analysis result (for example, the amount or type of the corrected information), the learning in the learning unit 304 and the update of the medical image identification engine may be executed.

(Flow of Processing in the Medical Support System)

Figure 2:
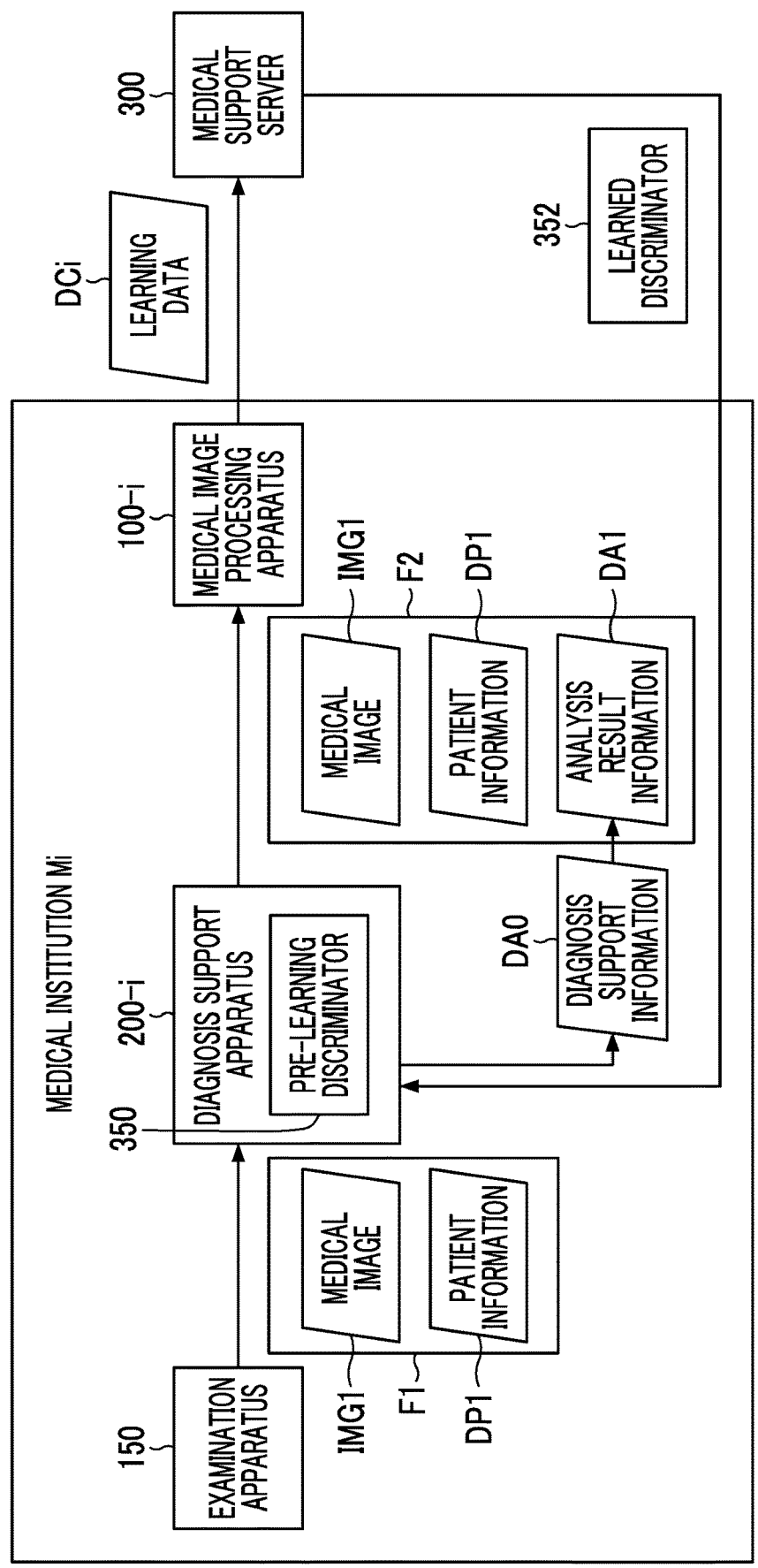
FIG. 2 is a block diagram for explaining a flow of processing in the medical support system according to the first embodiment of the present invention.
Figure 3:
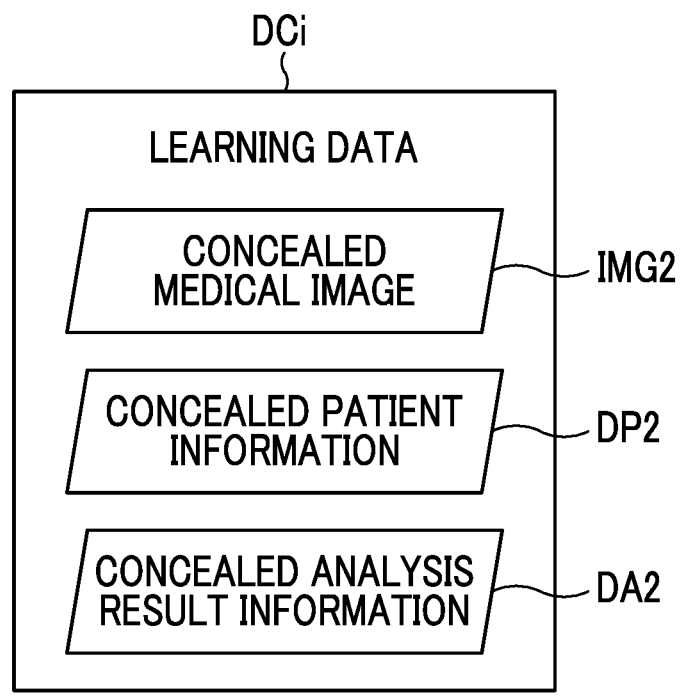
FIG. 3 is a data block diagram illustrating learning data according to the first embodiment of the present invention.

Next, a flow of processing in the medical support system will be specifically described with reference to FIGS. 2 and 3. FIG. 2 is a block diagram for explaining a flow of processing in the medical support system according to the first embodiment of the present invention, and FIG. 3 is a data block diagram illustrating the learning data.

An examination apparatus 150 illustrated in FIG. 2 is an apparatus for imaging an examination part of a patient in the medical institution Mi, for example, an X-ray imaging apparatus, a computed tomography (CT), a positron emission tomography (PET), a single photon emission computed tomography (SPECT), a magnetic resonance imaging (MRI), a mammography examination apparatus, or the like.

The examination apparatus 150 acquires a medical image IMG1 (for example, an X-ray image) by imaging the examination part of the patient. Further, the examination apparatus 150 comprises an input unit for receiving an input of patient information DPi (for example, patient identification information, patient ID, patient name, and the like) regarding the patient. The input unit of the examination apparatus 150 may include a keyboard for inputting characters. In addition, the input unit of the examination apparatus 150 may include a reading apparatus (for example, a magnetic card reader, an integrated circuit (IC) card reader) that reads information on a registration card of the patient and a searching unit for acquiring the patient information DPi from a hospital information systems (HIS) including a database in which information on patients of the medical institution Mi is housed using information on the registration card read by the reading apparatus.

The medical image IMG1 of the examination part of the patient and the patient information DPi acquired by the examination apparatus 150 are transmitted to the diagnosis support apparatus 200-*i*. Here, the medical image IMG1 and the patient information DPi can be created in a data format conforming to, for example, a digital imaging and communications in medicine (DICOM) or a medical image processing systems (MIPS) standard of Japan Medical Imaging and Radiological Systems Industries Association.

In the present embodiment, a file including the medical image IMG1 and the patient information DPi transmitted from the examination apparatus 150 to the diagnosis support apparatus 200-*i* is referred to as a DICOM file F1. The patient information DPi can be included in, for example, a tag or a private tag of the DICOM file F1. The private tag is a tag that can be independently defined by a modality maker (a maker of the examination apparatus 150 used for generating the medical image IMG1), and the like. The tag of the DICOM file will be described later (refer to tables 1 to 3).

The diagnosis support apparatus 200-$i$ acquires the medical image IMG1 and the patient information DPi of the examination part of the patient from the examination apparatus 150. The diagnosis support apparatus 200-$i$ analyzes the medical image IMG1 of the examination part of the patient using the pre-learning discriminator 350, and generates diagnosis support information DA0 including the analysis result. The diagnosis support information DA0 includes, for example, a result of region division of the examination part, an extraction result of a region and contour of the organ or bone included in the examination part, information such as whether or not the examination part includes a lesion, and in a case where a lesion is included, information such as the type of the lesion or a candidate for the type of lesion. The diagnosis support information DA0 is presented to the physician by a presentation unit (a display unit 210 or a physician terminal 220 in FIG. 7), and is used to assist the physician in making a diagnosis using the medical image IMG1.

Figure 7:
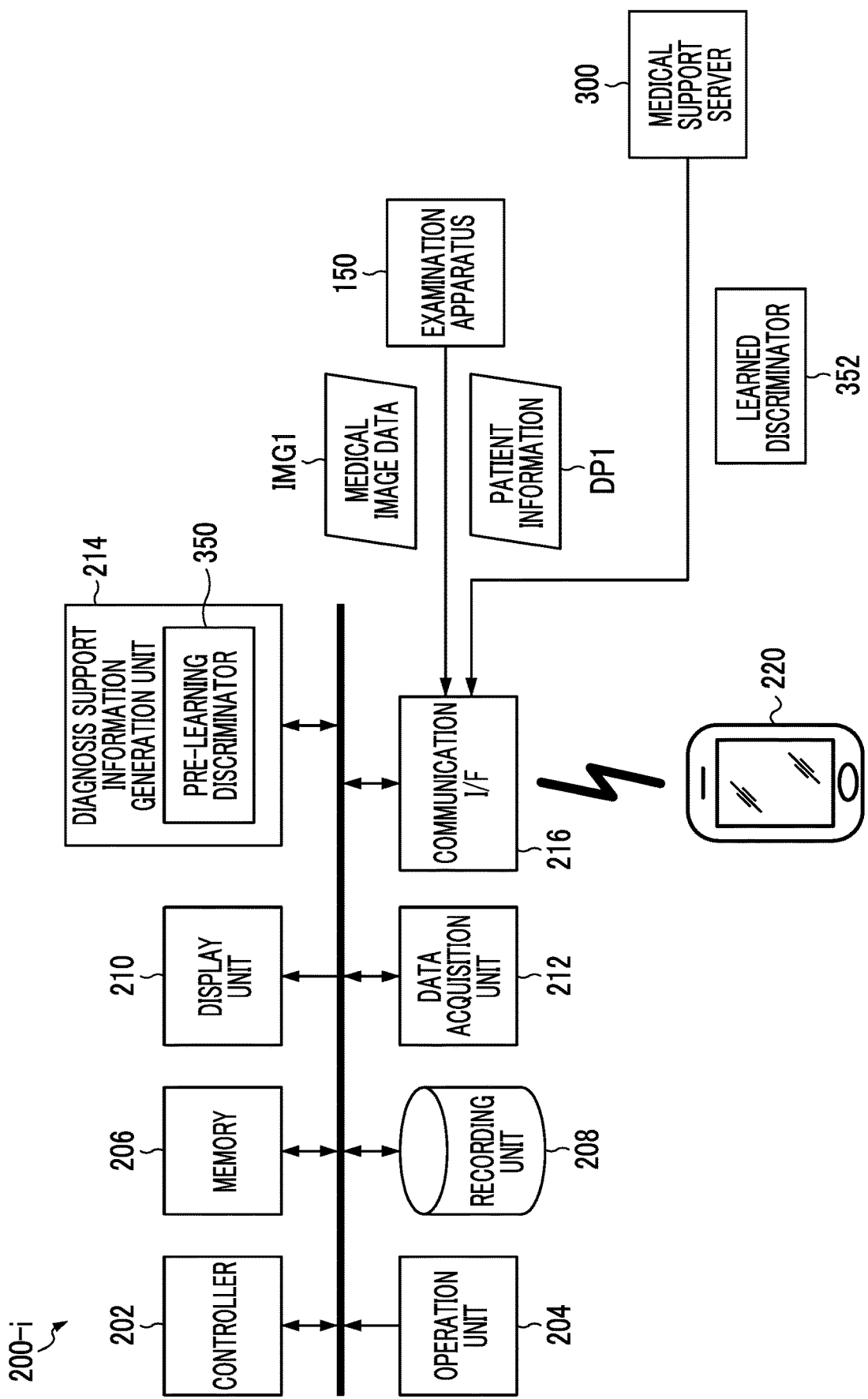
FIG. 7 is a block diagram illustrating a diagnosis support apparatus according to the first embodiment of the present invention.

The diagnosis support apparatus 200-$i$ comprises an operation input unit (of an operation unit 204 or an operation member of the physician terminal 220 in FIG. 7) that receives an input of approval or correction, and an input of selection of a candidate for the type of lesion included in the diagnosis support information DA0 for the analysis result included in the diagnosis support information DA0. The physician can interpret the medical image IMG1 while referring to the diagnosis support information DA0 presented on the presentation unit, and can approve and correct the diagnosis support information DA0 using the operation input unit.

In the diagnosis support apparatus 200-$i$, the diagnosis support information DA0 that has been approved or corrected by the physician is referred to analysis result information DA1. Additional information (for example, a flag and a parameter indicating the content or importance of the correction) indicating whether or not the diagnosis support information DA0 has been approved or corrected by the physician is added to the analysis result information DA1. In a case of receiving the input of the correction from the operation unit 204 or the physician terminal 220, the diagnosis support apparatus 200-$i$ (a controller 202 in FIG. 7) creates a DICOM file F2 by adding the analysis result information DA1 to the DICOM file F1. At this time, the analysis result information DA1 and the additional information (such as a flag indicating the presence or absence of correction) can be included in a tag or a private tag of the DICOM file F2. In addition, the analysis result information DA1 and the additional information (such as a flag indicating the presence or absence of correction) can be files different from the DICOM file F2. The diagnosis support apparatus 200-$i$ transmits the DICOM file F2 to the medical image processing apparatus 100-$i$.

For example, in a case of medical images of regions of heart and lung, the regions and contours of the heart and lung are extracted by the medical image identification engine to measure a cardio-thoracic ratio. In a case where an error is found in a detection result of regions of the heart and lung as a result of image interpretation by a physician, the physician corrects a marker indicating the regions or the contours of the heart and lung in the diagnosis support apparatus 200-$i$. The controller 202 of the diagnosis support apparatus 200-$i$ receives the input of the correction and generates the analysis result information DA1 in which a measured value of the regions of the corrected heart and lung and the cardio-thoracic ratio, and additional information indicating that the correction has been performed are housed.

In a case of extracting a region included in the medical image, the medical image identification engine determines the detection result of the range and contour of the region and property of the detection results. In a case where an error is found in the detection result of the range or contour of the region or the determination result of property thereof (for example, whether or not it is a tumor) as the result of image interpretation by a physician, the physician performs the correction in the diagnosis support apparatus 200-$i$. The controller 202 of the diagnosis support apparatus 200-$i$ receives the input of the correction and generates the analysis result information DA1 in which the corrected analysis result and the additional information indicating that the correction has been performed are housed. This analysis result information DA1 is used as correct answer data in learning of the medical image identification engine.

The medical image processing apparatus 100-$i$ acquires a DICOM file F2 including the medical image IMG1, the patient information DPi, and the analysis result information DA1 from the diagnosis support apparatus 200-$i$. Then, the medical image processing apparatus 100-$i$ performs concealment processing for concealing identification information that can identify a patient for the medical image IMG1, the patient information DPi, and the analysis result information DA in which approval or correction has been input by the physician to generate the learning data DCi.

As illustrated in FIG. 3, the learning data DCi includes a concealed medical image IMG2, patient information DP2, and analysis result information DA2. Similarly to the DICOM files F1 and F2, the learning data DCi can be created in a data format conforming to, for example, a digital imaging and communications in medicine (DICOM) or a medical image processing systems (MIPS) standard of Japan Medical Imaging and Radiological Systems Industries Association.

The learning data DCi can be used, for example, as teacher data for supervised learning that inputs the image of an examination part of a patient extracted from the medical image and outputs data that include analysis result information for the examination part of the patient and have been approved or corrected by the physician. The "output" in the teacher data may be called a teacher signal, a teaching signal, correct answer data, or a label.

The medical image processing apparatus 100-$i$ transmits the learning data DCi to the medical support server 300. The data collecting and housing unit 302 of the medical support server 300 collects the learning data DC1, DC2, . . . , DCn respectively transmitted from the medical image processing apparatus 100-1, 100-2, . . . , 100-$n$ of the medical institutions M1, M2, . . . , Mn.

The learning unit 304 of the medical support server 300 causes the pre-learning discriminator 350 to perform learning using the learning data DC1, DC2, . . . , DCn collected from the medical institutions M1, M2, . . . , Mn.

In the learning unit 304, for example, a medical image of the examination part of the patient read out from the learning data DC1, DC2, . . . , DCn which is the teacher data, and feature quantity in the medical image are input to the pre-learning discriminator 350. Then, the learning unit 304 performs learning on the input medical image of the examination part so as to obtain the same output as information indicating the diagnosis result corresponding to the examination part. Here, as the feature quantity in the medical image, for example, the average of brightness or luminance in the medical image, the area of the examination part or lesion, the perimeter and the flatness, and the length of the long axis in a case where the examination part or lesion is approximated to an ellipse, and the inclination of the long axis with respect to the examination part of the patient or a feature part of the lesion (for example, contours of spine, bones or internal organs included in the examination part of the patient, center of gravity or central axis) can be used.

The pre-learning discriminator 350 and the learned discriminator 352 are data used for generating the diagnosis support information in the diagnosis support apparatus 200-i, and includes, for example, information indicating the structure of the diagnosis support apparatus 200-1, 200-2, . . . , 200-n (a diagnosis support information generation unit 214) and a value of a variable. As the pre-learning discriminator 350 and the learned discriminator 352, for example, those using a neural network, deep learning, a decision tree, a linear classifier, a support vector machine (SVM), a discriminant analysis, and the like can be used.

The diagnosis support apparatus 200-i acquires the learned discriminator 352 from the medical support server 300, and updates the medical image identification engine.

In a case where another medical image (a medical image that has not been used for learning, for example, a medical image of a patient to be newly examined) is acquired by the examination apparatus 150, the diagnosis support apparatus 200-i analyzes the another medical image using the learned discriminator 352. Then, the diagnosis support apparatus 200-i generates diagnosis support information indicating an analysis result of another medical image, and presents it to the physician of the medical institution Mi.

The medical image processing apparatus 100-1, 100-2, . . . , 100-n, the diagnosis support apparatus 200-1, 200-2, . . . , 200-n, and the medical support server 300 can be communicated via a network, but the present invention is not limited to thereto. For example, an administrator of the medical support server 300 may visit each of the medical institutions M1, M2, . . . , Mn to collect the learning data DC1, DC2, . . . , DCn and provide the learned discriminator 352 (the update of the medical image identification engine) to the diagnosis support apparatus 200-1, 200-2, . . . , 200-n.

In the present embodiment, the medical image processing apparatus 100-i and the diagnosis support apparatus 200-i are separate apparatuses, but they may be the same apparatus.

Further, the medical image processing apparatus 100-i and the diagnosis support apparatus 200-i according to the present embodiment may be included in PACS (Picture Archiving and Communication Systems) in the medical institution Mi.

(Medical Image Processing Apparatus)

Figure 4:
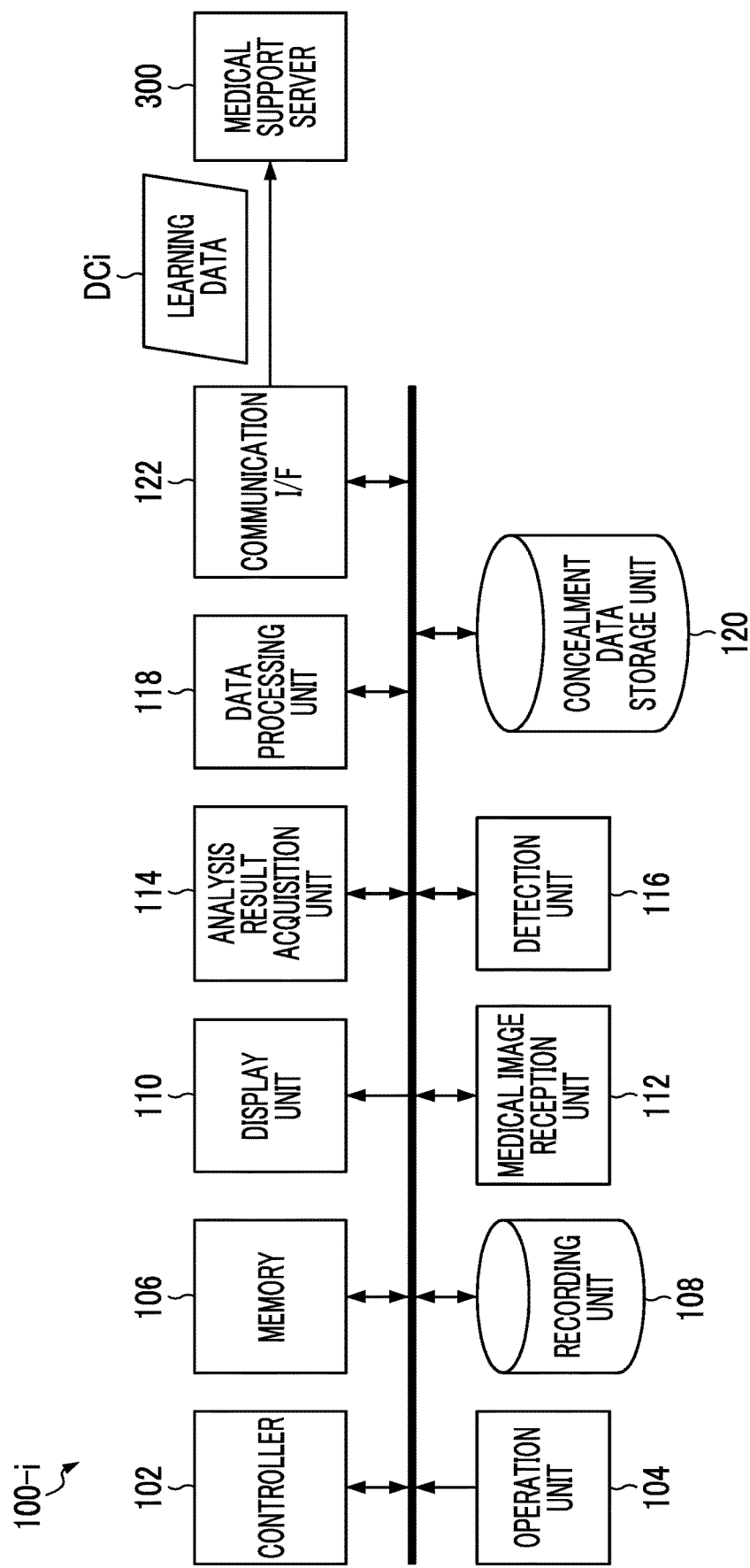
FIG. 4 is a block diagram illustrating a medical image processing apparatus according to the first embodiment of the present invention.

Next, the medical image processing apparatus will be described with reference to FIG. 4. FIG. 4 is a block diagram illustrating a medical image processing apparatus according to the first embodiment of the present invention.

The medical image processing apparatus 100-i according to the present embodiment includes a controller 102, an operation unit 104, a memory 106, a recording unit 108, a display unit 110, a medical image reception unit 112, an analysis result acquisition unit 114, a detection unit 116, a data processing unit 118, a learning data storage unit 120, and a communication interface (communication I/F: interface) 122.

The controller 102 includes a central processing unit (CPU) that controls the operation of each unit of the medical image processing apparatus 100-i. The controller 102 is capable of transmitting and receiving control signals and data to and from each unit of the medical image processing apparatus 100-i via a bus. The controller 102 receives an operation input from an operator (physician or the like) via the operation unit 104, and controls the operation of each unit by transmitting a control signal corresponding to the operation input to each unit of the medical image processing apparatus 100-i via the bus.

The operation unit 104 is an input apparatus that receives the operation input from the operator, and includes a keyboard for inputting characters and the like, and a pointing device (for example, a mouse, a trackball, or the like) for operating a pointer, an icon, or the like displayed on the display unit 110. As the operation unit 104, a touch panel may be provided on the surface of the display unit 110 instead of the keyboard and the pointing device, or in addition to the keyboard and the pointing device.

The memory 106 includes a random access memory (RAM) used as a work area for various calculations performed by the controller 102 and the like, and a video random access memory (VRAM) used as a region for temporarily storing the image data output to the display unit 110.

The recording unit 108 is a storage device that houses a control program used by the controller 102, data (DICOM file F2) received from the diagnosis support apparatus 200-i, and the like. As the recording unit 108, for example, an apparatus including a magnetic disk such as a hard disk drive (HDD), an apparatus including a flash memory such as an embedded multi media card (eMMC), a solid state drive (SSD), or the like can be used.

The display unit 110 is an apparatus for displaying an image. As the display unit 110, for example, a liquid crystal monitor can be used.

The communication I/F 122 is a unit for communicating with another apparatus via a network, and performs conversion processing of data to be transmitted and received according to a communication method. As a method of transmitting and receiving data between the medical image processing apparatus 100-i and another apparatus, wired communication or wireless communication (for example, local area network (LAN), wide area network (WAN), internet connection, and or the like) can be used.

The medical image reception unit 112 receives the input of the medical image IMG1 and the patient information DPi from the DICOM file F2 transmitted from the diagnosis support apparatus 200-i. The medical image IMG1 and the like input to the medical image reception unit 112 are images that have been interpreted by a physician in the diagnosis support apparatus 200-i.

The analysis result acquisition unit 114 acquires the analysis result information DA1 from the DICOM file F2 transmitted from the diagnosis support apparatus 200-i.

The detection unit 116 determines whether or not the analysis result information DA1 includes additional information indicating that the diagnosis support information DA0 has been approved or corrected in the diagnosis support apparatus 200-i. Then, the detection unit 116 outputs a DICOM file F2 including the additional information indicating that the approval or the correction has been performed to the data processing unit 118. That is, in the present embodiment, a DICOM file F2 that has not been approved or corrected by the physician is not used for creating the learning data DCi.

In the present embodiment, all DICOM files F2 are used for creating the learning data DCi regardless of whether or not the diagnosis support information DA0 is corrected, but the present invention is not limited to thereto. For example, the detection unit 116 may be used for creating the learning data DCi only for the DICOM file F2 including the additional information indicating that the diagnosis support information DA0 has been corrected, that is, for those in which an error is found in the analysis result by the pre-learning discriminator 350. In this case, it is possible to selectively use a medical image that greatly contributes to improving the accuracy of the diagnosis using the medical image, so that it is possible to perform learning effectively and efficiently. Further, it is possible to improve the contribution degree of the medical institution Mi by selecting the medical image that greatly contributes to improving the accuracy of the diagnosis using the medical image and creating the learning data DCi.

In addition, in the present embodiment, additional information indicating the presence or absence of approval or correction is added to the analysis result information DA1, but the present invention is not limited to thereto. For example, without using the additional information, the detection unit 116 may acquire both the diagnosis support information DA0 and the analysis result information DA1 and compare these to determine whether or not the correction is performed.

The data processing unit 118 performs concealment processing on the DICOM file F2 for concealing patient identification information. Then, the data processing unit 118 generates the learning data DCi including the concealed medical image IMG2, patient information DP2, and analysis result information DA2.

The learning data storage unit 120 is a storage device that stores the learning data DCi that has been subjected to the concealment processing of the patient identification information by the data processing unit 118. The learning data storage unit 120 may be, for example, a storage region provided in the recording unit 108.

In the present embodiment, the learning data DCi is transmitted to the medical support server 300 after being stored in the learning data storage unit 120 of the medical image processing apparatus 100-$i$, but the present invention is not limited to thereto. The learning data storage unit 120 may be, for example, provided on a cloud where the learning data DCi can be uploaded from the medical image processing apparatus 100-$i$ and the data collecting and housing unit 302 of the medical support server 300 can download the learning data DCi. In this case, for example, a cloud-type VPN can be used.

(Concealment Processing)

Next, the concealment processing by the data processing unit 118 will be described. First, the concealment processing for the patient information DPi will be described.

In the present embodiment, the patient information DPi is housed as tag information in the DICOM file F2. The data processing unit 118 deletes identification information that can identify a patient from the tag information of the DICOM file F2.

Tables 1 to 3 show examples of the tags of the DICOM file. Table 1 shows an example of a tag related to patient identification information, Table 2 shows an example of a tag related to a medical institution Mi, and Table 3 shows an example of a tag related to the content of an examination.

The data processing unit 118 deletes the tags related to the patient identification information shown in Table 1 other than those including information necessary for analyzing the medical image IMG1. For example, among the tags in Table 1, tags such as age of the patient, smoking status, additional medical history of the patient, and pregnancy status may be left. All tags related to the patient identification information shown in Table 1 may be deleted.

TABLE 1

Example of Tag related to Patient Identification Information

| Tag | Title |
|---|---|
| (0010, 0020) | Patient ID |
| (0010, 0010) | Patient's Name |
| (0010, 0030) | Patient's Birth Date |
| (0010, 0032) | Patient's Birth Time |
| (0010, 0040) | Patient's Sex |
| (0010, 1010) | Patient's Age |
| (0010, 1020) | Patient's Size |
| (0010, 1030) | Patient's Weight |
| (0010, 1040) | Patient's Address |
| (0010, 2154) | Patient's Telephone Numbers |
| (0010, 2180) | Occupation |
| (0010, 2160) | Ethnic Group |
| (0010, 2000) | Medical Alerts |
| (0010, 2110) | Allergies |
| (0010, 21A0) | Smoking Status |
| (0010, 21B0) | Additional Patient History |
| (0010, 21C0) | Pregnancy Status |
| (0010, 4000) | Patient Comments |

TABLE 2

Example of Tag related to Medical Institution

| Tag | Title |
|---|---|
| (0008, 0080) | Institution Name |
| (0008, 0081) | Institution Address |

Further, the data processing unit 118 may consider that the patient identification information is included in tags such as a reception number, an examination description, and a diagnosis description at the time of consultation among tags related to the content of the examination. Therefore, the data processing unit 118 acquires the patient identification information (for example, patient ID, patient name, birthday, address, telephone number, occupation, and the like), and compares it with tag information such as the examination description and the diagnosis description at the time of consultation. Thereafter, in a case where the patient identification information is included, the data processing unit 118 deletes the entire tag information or replaces the patient information included in the tag information with a hidden character. The data processing unit 118 may manually delete the information after a physician or an operator of the medical institution Mi checks the content of the tag.

TABLE 3

Example of Tag related to Content of Examination

| Tag | Title |
|---|---|
| (0008, 1040) | Institutional Department Name |
| (0008, 0050) | Accession Number |
| (0008, 0020) | Study Date |
| (0008, 0030) | Study Time |
| (0008, 0060) | Modality |
| (0008, 0070) | Manufacturer |
| (0018, 0015) | Body Part Examined |
| (0010, 9431) | Examined Body Thickness |
| (0008, 1030) | Study Description |
| (0008, 1080) | Admitting Diagnoses Description |
| (0008, 1048) | Physician(s) of Record |
| (0008, 1050) | Performing Physician's Name |

TABLE 3-continued

Example of Tag related to Content of Examination

| Tag | Title |
|---|---|
| (0008, 1060) | Name of Physician(s) Reading Study |
| (0008, 1070) | Operator's Name |

In addition, it is conceivable that a private tag also includes the patient identification information. Therefore, the data processing unit 118 acquires the patient identification information (for example, patient ID, patient name, address, telephone number, and the like), and compares it with the content of the private tag. Thereafter, in a case where the patient identification information is included, the data processing unit 118 deletes the entire tag information or replaces the patient information included in the tag information with a hidden character. The data processing unit 118 may delete all the private tags, or may manually delete the information after the physician or the operator of the medical institution Mi checks the content of the private tag.

Figure 5:
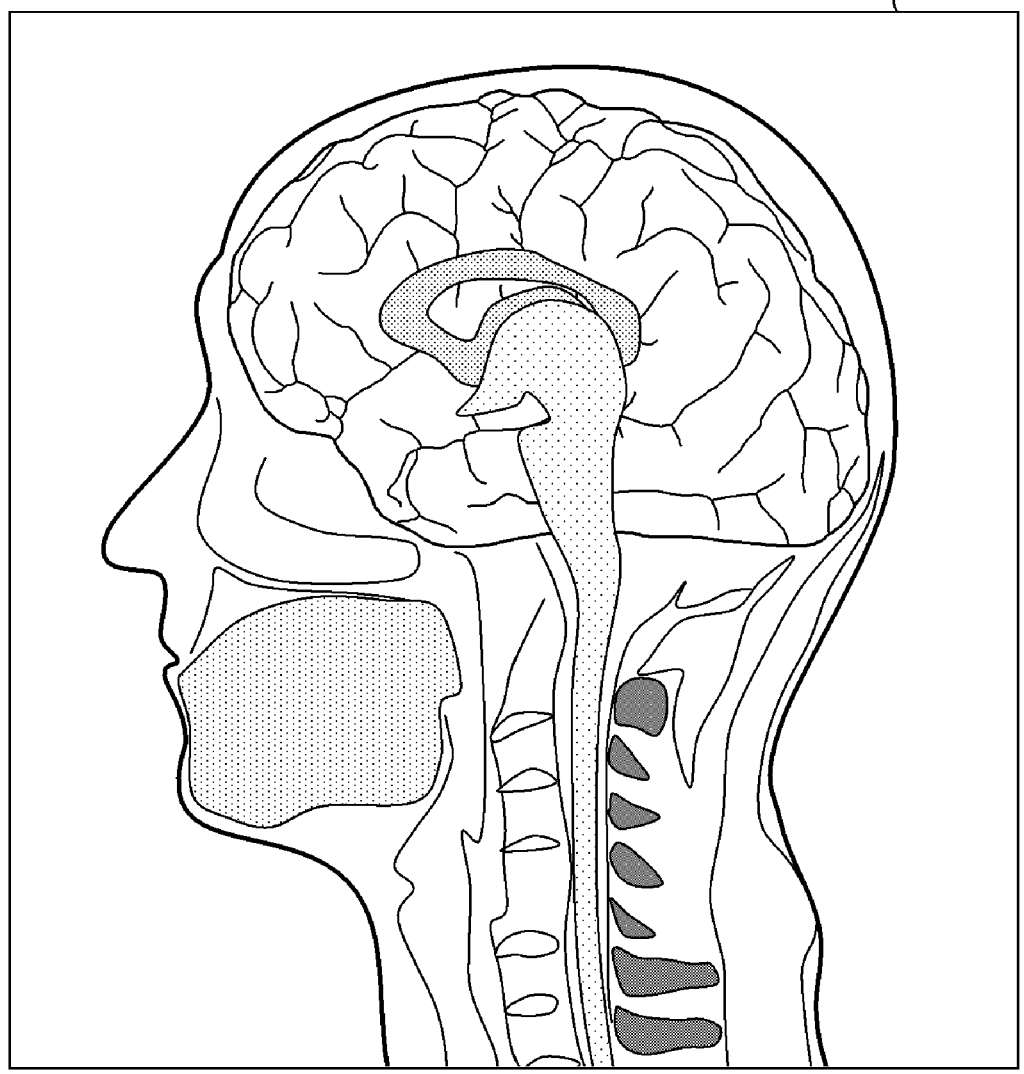
FIG. 5 is a diagram illustrating an example of medical images.

Next, the concealment processing of the patient identification information from the medical image will be described with reference to FIGS. 5 and 6. FIG. 5 illustrates an example of a medical image, and FIG. 6 illustrates an example of a concealed medical image.

The medical image IMG1 illustrates in FIG. 5 is a tomographic image of the patient's head and includes a part of a body surface. In a case where the part of the body surface is extracted from a plurality of tomographic images and combined, a patient's face is reproduced.

Figure 6:
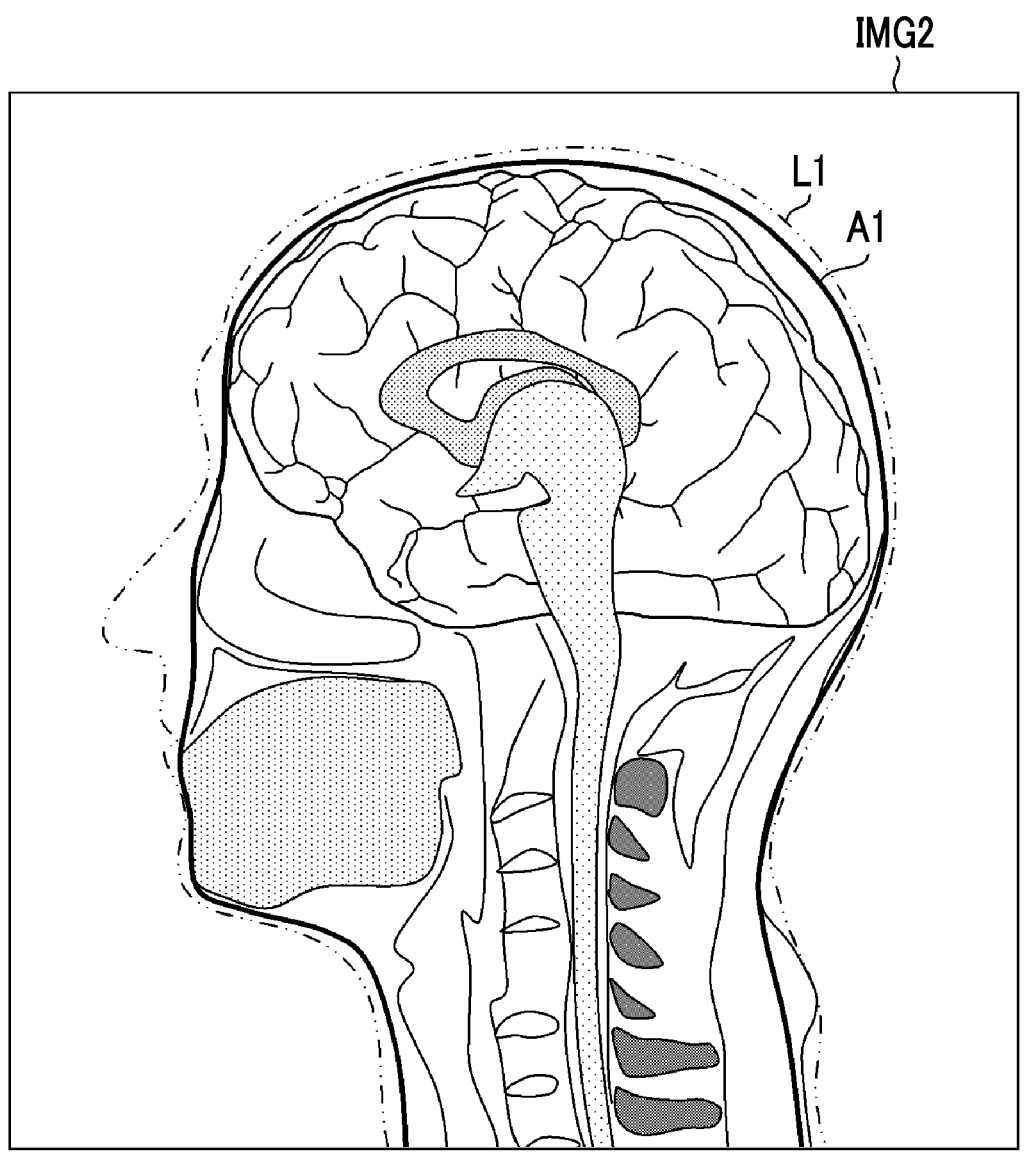
FIG. 6 is a diagram illustrating an example of a concealed medical image.

Therefore, as illustrated in FIG. 6, the data processing unit 118 processes the medical image IMG1 and deletes a region A1 near a body surface L1 to create a concealed medical image IMG2 in which body surface data is concealed. Here, the region A1 near the body surface L1 can be, for example, a region from the body surface L1 to a contour of a tissue to be diagnosed (for example, brain, trachea, bone, or the like). The data processing unit 118 performs a process of filling the region A1 with the same color as the background color or overlapping another image. This makes it possible to conceal the image of the body surface of the patient.

In the learning data DCi, the patient identification information is encrypted and housed, and in a case where it is necessary for diagnosis and learning, an operator who has access authority to the patient identification information may be able to retrieve the patient information DPi. In addition, an electronic signature may be added to the learning data DCi in order to enable tampering detection.

(Diagnosis Support Apparatus)

Next, the diagnosis support apparatus will be described with reference to FIG. 7. FIG. 7 is a block diagram illustrating a diagnosis support apparatus according to the first embodiment of the present invention.

The diagnosis support apparatus 200-*i* according to the present embodiment includes the controller 202, the operation unit 204, a memory 206, a recording unit 208, the display unit 210, a data acquisition unit 212, a diagnosis support information generation unit 214, and a communication interface (communication I/F: interface) 216.

The controller 202 includes a central processing unit (CPU) that controls the operation of each unit of the diagnosis support apparatus 200-*i*. The controller 202 is capable of transmitting and receiving control signals and data to and from each unit of the diagnosis support apparatus 200-*i* via a bus. The controller 202 receives an operation input from an operator via the operation unit 104, and controls the operation of each unit by transmitting a control signal corresponding to the operation input to each unit of the diagnosis support apparatus 200-*i* via the bus.

The operation unit 204 is an input apparatus that receives the operation input from the operator, and includes a keyboard for inputting characters and the like, and a pointing device (for example, a mouse, a trackball, or the like) for operating a pointer, an icon, or the like displayed on the display unit 210. As the operation unit 204, a touch panel may be provided on the surface of the display unit 210 instead of the keyboard and the pointing device, or in addition to the keyboard and the pointing device.

The memory 206 includes a random access memory (RAM) used as a work area for various calculations performed by the controller 202 and the like, and a video random access memory (VRAM) used as a region for temporarily storing the image data output to the display unit 210.

The recording unit 208 is a storage device that houses a control program used by the controller 202, data (DICOM file F1) received from the examination apparatus 150, and the like. As the recording unit 208, for example, an apparatus including a magnetic disk such as a hard disk drive (HDD), an apparatus including a flash memory such as an embedded multi media card (eMMC), a solid state drive (SSD), or the like can be used.

The display unit 210 is an apparatus for displaying an image. As the display unit 210, for example, a liquid crystal monitor can be used.

A communication I/F 216 is a unit for communicating with another apparatus via a network, and performs conversion processing of data to be transmitted and received according to a communication method. As a method of transmitting and receiving data between the medical image processing apparatus 100-*i* and another apparatus, wired communication or wireless communication (for example, local area network (LAN), wide area network (WAN), internet connection, and or the like) can be used.

The physician terminal 220 is a terminal for a physician of the medical institution Mi to display data such as medical images and to perform an operation input. The physician terminal 220 acquires and displays the data such as medical images from the diagnosis support apparatus 200-*i* via the communication I/F 216, and receives the operation input from the physician. Thereby, the physician terminal 220 can perform processing and an update of the data of the diagnosis support apparatus 200-*i*.

The data acquisition unit 212 acquires the DICOM file F1 including the medical image IMG1 of the patient and the patient information DP1 from the examination apparatus 150.

The diagnosis support information generation unit 214 analyzes the medical image IMG1 using the medical image identification engine (the pre-learning discriminator 350 or the learned discriminator 352), generates diagnosis support information DA0 including the analysis result, and causes the display unit 210 to display it with the medical image IMG1 and the patient information DPi. Thereby, the physician can interpret the medical image IMG1 while referring to the diagnosis support information DA0.

(Medical Image Processing Method)

Figure 8:
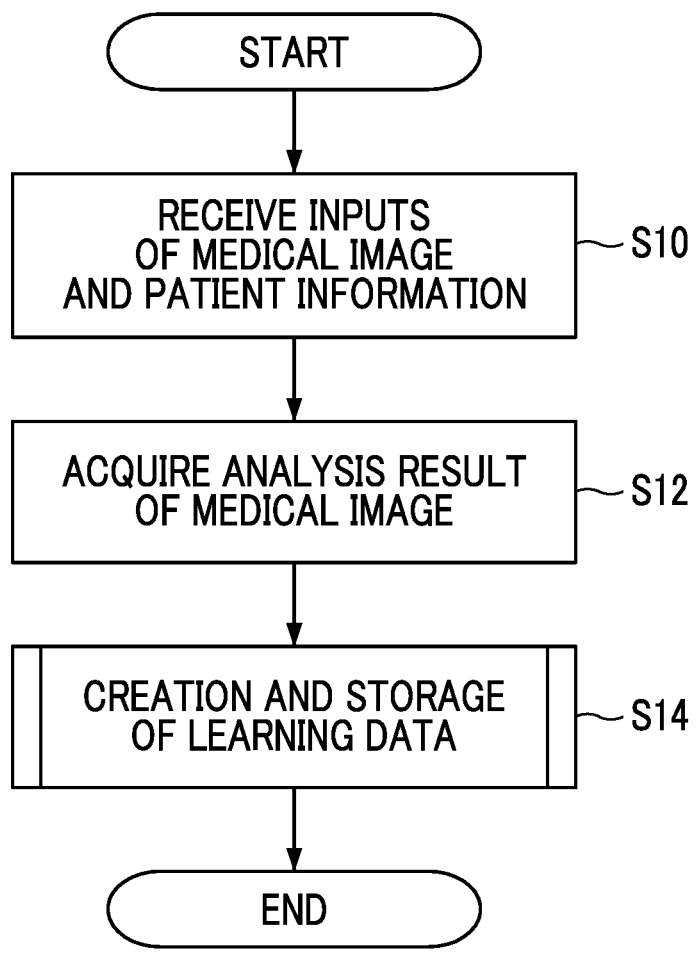
FIG. 8 is a flowchart illustrating a flow of processing in a medical image processing method according to the first embodiment of the present invention.

Next, the medical image processing method according to the present embodiment will be described with reference to FIG. 8. FIG. 8 is a flowchart illustrating a flow of processing in a medical image processing method according to the first embodiment of the present invention.

First, the medical image processing apparatus 100-i acquires the DICOM file F2 including the medical image IMG1 interpreted by the physician and the analysis result information DA1 in which the diagnosis support information DA0 has been approved or corrected by the physician from a diagnosis support apparatus 200-i. The medical image reception unit 112 receives inputs of the medical image IMG1 and the patient information DPi (step S10: reception step). The analysis result acquisition unit 114 acquires the analysis result information DA1 of the medical image IMG1 (step S12: analysis result information step).

Next, the data processing unit 118 performs concealment processing on the DICOM file F2 to create the learning data DCi, and stores the concealment data DCi in the learning data storage unit 120 (step S14: data processing step).

(Diagnosis Support Method)

Figure 9:
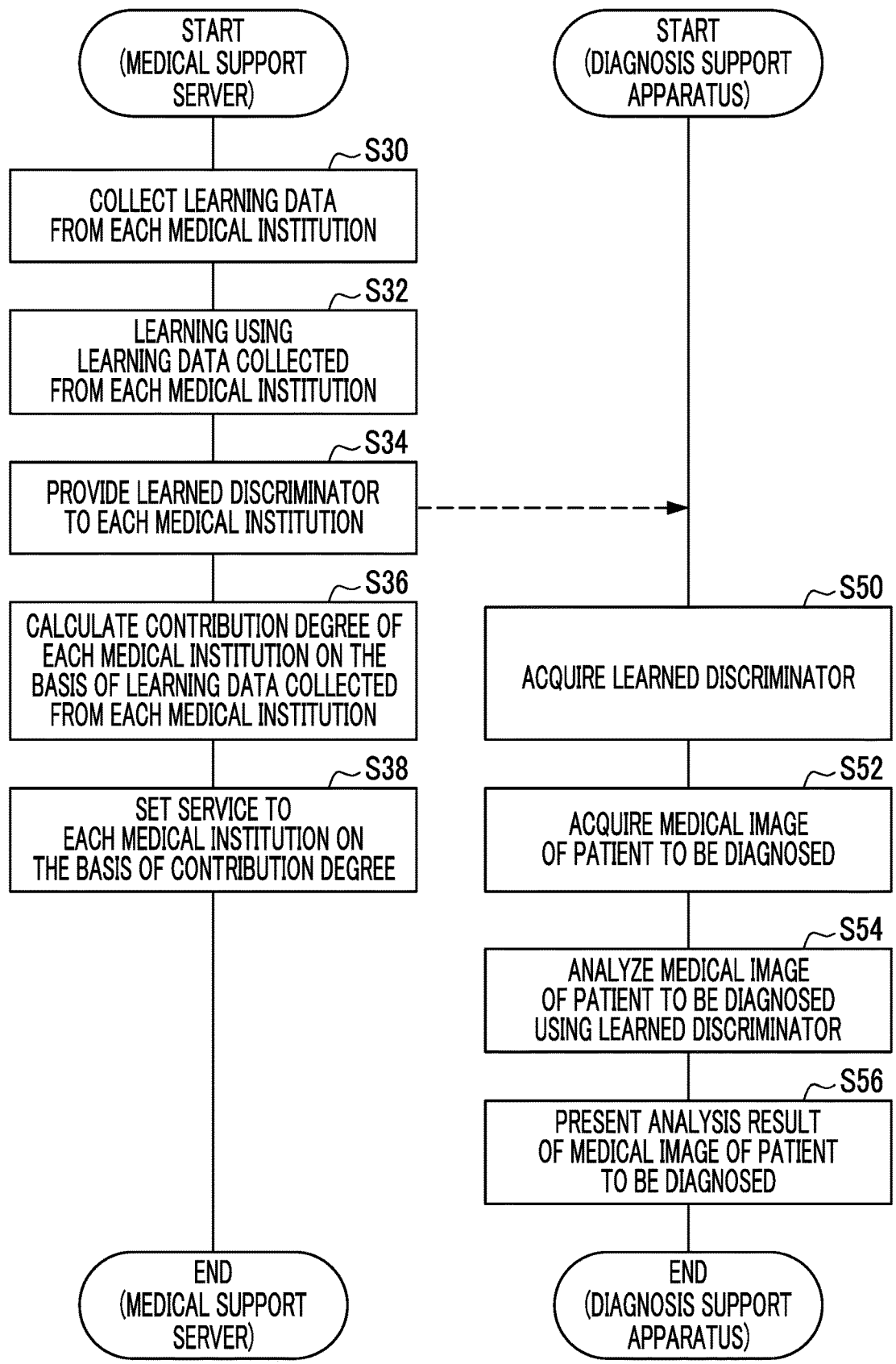
FIG. 9 is a flowchart illustrating a flow of processing in a diagnosis support method according to the first embodiment of the present invention.

Next, the diagnosis support method (including a learning method) according to the present embodiment will be described with reference to FIG. 9. FIG. 9 is a flowchart illustrating a flow of processing in a diagnosis support method according to the first embodiment of the present invention.

First, in the medical support server 300, the data collecting and housing unit 302 collects learning data DC1, DC2, ..., DCn respectively from the medical institutions M1, M2, ..., Mn (step S30).

Next, the learning unit 304 causes the medical image identification engine (the pre-learning discriminator 350) to perform learning using the learning data DC1, DC2, ..., DCn collected respectively from the medical institutions M1, M2, ..., Mn (step S32). Then, the learned discriminator 352 is provided from the medical support server 300 to the medical institutions M1, M2, ..., Mn (step S34).

Next, the diagnosis support apparatus 200-i updates the medical image identification engine by acquiring the learned discriminator 352 from the medical support server 300 via the communication I/F 216 and replacing it with the pre-learning discriminator 350 of the diagnosis support information generation unit 214 (step S50).

Next, in a case where the data acquisition unit 212 of a diagnosis support apparatus 200A-i acquires a medical image of a patient to be diagnosed from the examination apparatus 150 (step S52), the diagnosis support information generation unit 214 analyzes the medical image of the patient to be diagnosed using the learned discriminator 352 (step S54). Then, the diagnosis support information generation unit 214 presents the analysis result of the medical image of the patient to be diagnosed as diagnosis support information DA0, that is, causes the display unit 210 to display the analysis result (step S56). In addition, a method of presenting the diagnosis support information DA0 is not limited to display, and may be, for example, printing.

In the medical support server 300, the contribution degree of each medical institution Mi is calculated. First, the calculation unit 306 of the medical support server 300 calculates the contribution degree of each medical institution Mi on the basis of the learning data DCi collected from each medical institution Mi (step S36).

Next, the service setting unit 308 sets service to be provided to each medical institution Mi on the basis of the contribution degree of each medical institution Mi calculated in step S36 (step S38).

In the present embodiment, the collection and learning of the learning data DCi by the medical support server 300 and the evaluation and service setting of the learning data DCi are performed at the same timing, but the present invention is not limited to thereto. The evaluation of the learning data DCi and the service setting may be, for example, performed periodically. In addition, the evaluation and the service setting of the learning data DCi may be performed, for example, in a case where the number of accumulated medical images is equal to or more than a predetermined number, on the basis of the data amount of learning data DCi collected from all medical institutions Mi that are users (Calculation of Contribution Degree)

Next, a method of calculating the contribution degree will be described. The following methods can be considered as the method of calculating the contribution degree.

(A) A contribution degree of a medical institution Mi is calculated on the basis of a comparison result between the output obtained by inputting learning data DCi (first learning data) to a pre-learning discriminator 350 and concealed analysis result information DA2 (correct answer data) corresponding to the learning data DCi, (B) A contribution degree of a medical institution Mi is calculated on the basis of a comparison result between learning data DCi and second learning data used for creating a pre-learning discriminator 350.

(C) A contribution degree of a medical institution Mi is calculated on the basis of a degree of accuracy improvement in a learned discriminator 352 after learning is performed using learning data DCi.

Of the methods of calculating the contribution degree, (A) can be used for calculating the contribution degree before and after causing the pre-learning discriminator 350 to perform learning. (B) and (C) can be used for calculating the contribution degree after causing the pre-learning discriminator 350 to perform learning.

(Method (A) of Calculating Contribution Degree)

First, specific examples (example A-1 and example A-2) of the method (A) of calculating the contribution degree will be described.

Example A-1

Figure 10:
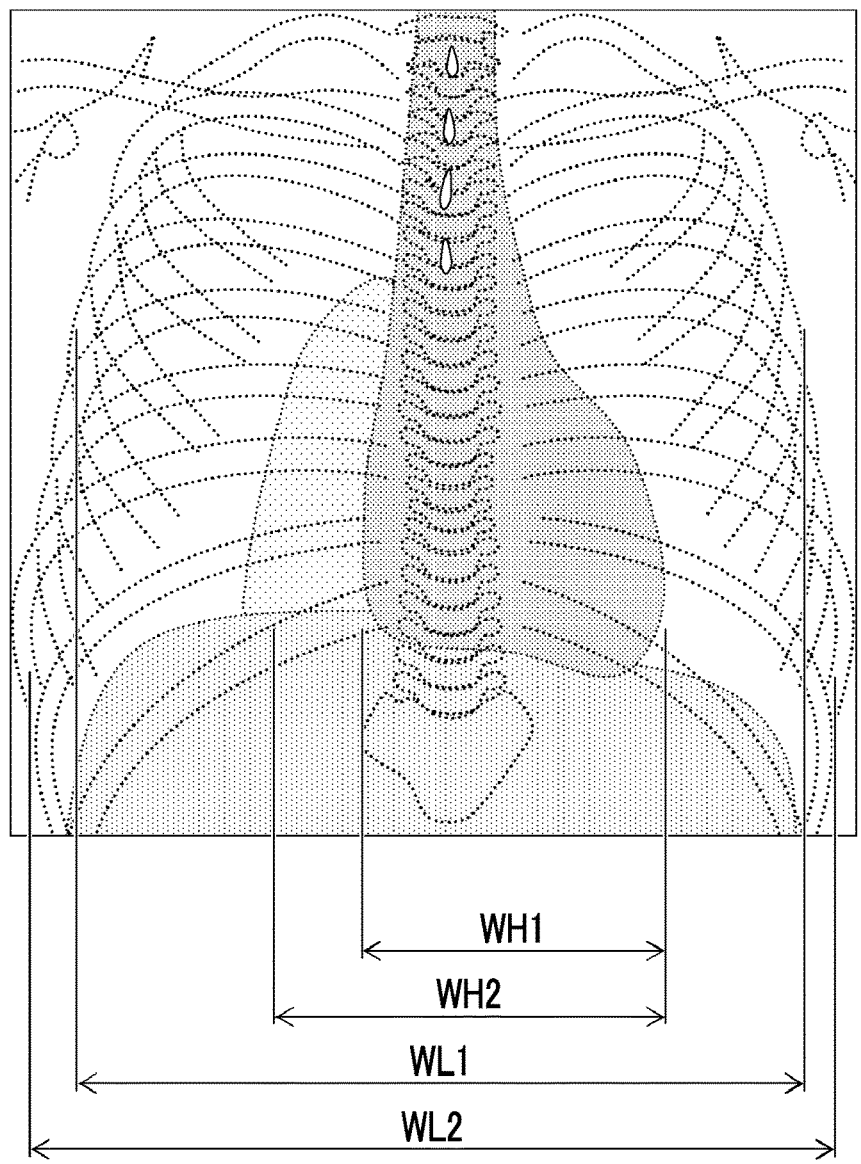
FIG. 10 is a diagram illustrating an example of medical images.

Example A-1 describes a case where a medical image identification engine for measuring a cardio-thoracic ratio is used. FIG. 10 is a diagram illustrating an example (chest X-ray image) of medical images.

In this example, the diagnosis support information generation unit 214 analyzes the medical images (chest X-ray image) using the pre-learning discriminator 350, automatically extracts regions of the heart and lung (lung field region), and measures the cardio-thoracic ratio. A result of extracting the heart region and the lung field region by the diagnosis support information generation unit 214 is displayed on the display unit 210 or the display screen of the physician terminal 220 as the diagnosis support information DA0. Specifically, as illustrated in FIG. 10, the result of extracting the heart region and the lung field region is superimposed on the chest X-ray image and is displayed as instruction lines indicating the left and right ends (boundary) of the extracted lung field region and the left and right ends (boundary) of the heart region, respectively. This instruction lines are, for example, a straight line or a line segment along the machine direction of the medical image, and is substantially parallel to the standing direction or spine direction of a patient.

A physician observes the display of the instruction lines and, in a case where it is determined that the instruction lines are located at the boundary of the heart region or the lung field region, operates the operation unit 204 or an operation member of the physician terminal 220 to input the approval of the extraction result. In a case of receiving the input of the approval from the operation unit 204 or the like, the controller 202 generates the analysis result information DA1 (correct answer data) by adding additional information indicating that it has been approved by the physician to the diagnosis support information DA0.

On the other hand, the physician observes the display of the instruction lines and, in a case where it is determined that the instruction lines are deviated from the boundary of the heart region or the lung field region, operates the operation unit 204 or the operation member of the physician terminal 220 to correct the position to a correct position. In a case of receiving the input of the correction from the operation unit 204 or the like, the controller 202 generates the analysis result information DA1 (correct answer data) by adding the additional information indicating that it has been approved by the physician and a contribution degree parameter P1 by the correction to position information of the corrected instruction lines.

In example A-1, the contribution degree parameter P1 can be calculated as follows. As illustrated in FIG. 10, the widths of the heart regions before and after the correction are set to WH1 and WH2, respectively, and the widths of the lung field regions before and after the correction are set to WL1 and WL2, respectively. At this time, the contribution degree parameter P1 is set to P1=|(WH2−WH1)/WH1|+|(WL2−WL1)/WL1|. The contribution degree parameter P1 is a value proportional to the correction amount by the physician, and has a correlation with a magnitude of the error of the pre-learning discriminator 350. The parameter P1 is housed in the analysis result information DA1, and also housed in the concealed analysis result information DA2. The concealed analysis result information DA2 is housed in the learning data DCi and sent to the medical support server 300.

The calculation unit 306 of the medical support server 300 reads out the contribution degree parameter P1 from the learning data DCi and adds it to the contribution degree of the medical institution Mi. Thereby, the contribution degree parameter P1 having the correlation with the magnitude of the error of the pre-learning discriminator 350 can be reflected on the contribution degree of the medical institution Mi, so that the contribution degree of the learning data DCi can be appropriately evaluated.

Example A-2

Figure 11:
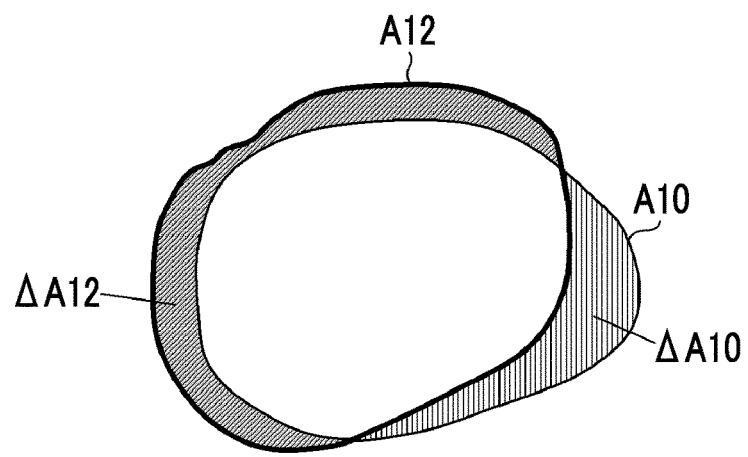
FIG. 11 is a diagram illustrating another example of medical images.

Example A-2 describes a case where a medical image identification engine for extracting a region of a predetermined organ (for example, a tumor) from a medical image is used. FIG. 11 is a diagram illustrating an example (CT image) of medical images.

In this example, the diagnosis support information generation unit 214 analyzes the medical image (CT image) using the pre-learning discriminator 350, and automatically extracts a tumor region. A result of extracting the tumor region by the diagnosis support information generation unit 214 is displayed on the display unit 210 or the display screen of the physician terminal 220 as the diagnosis support information DA0. Specifically, as illustrated in FIG. 11, the detection result of the tumor region is superimposed on the CT image and displayed as a curve (closed curve) surrounding an extracted tumor region A10.

A physician observes the display of the closed curve and, in a case where it is determined that the closed curve correctly indicates a boundary of the tumor region, operates the operation unit 204 or the operation member of the physician terminal 220 to input the approval of the extraction result. In a case of receiving the input of the approval from the operation unit 204 or the like, the controller 202 generates the analysis result information DA1 (correct answer data) by adding additional information indicating that it has been approved by the physician to the diagnosis support information DA0.

On the other hand, the physician observes the display of the closed curve, in a case where it is determined that the closed curve is deviated from the boundary of the tumor region, operates the operation unit 204 or the operation member of the physician terminal 220 to correct the position to a correct position. In a case of receiving the input of the correction from the operation unit 204 or the like, the controller 202 generates the analysis result information DA1 (correct answer data) by adding the additional information indicating that it has been approved by the physician and a contribution degree parameter P2 by the correction to position information of the corrected instruction lines.

In example 2, the contribution degree parameter P2 can be calculated as follows. As illustrated in FIG. 11, the area of the tumor region A10 before the correction is set to $S_{A10}$, the area of a part of the tumor region A10 before the correction that is excluded from a tumor region A12 after the correction is set to $\Delta A10$, and the area of a part added to the tumor region A10 after the correction is set to $\Delta A12$ compared to the tumor region A10 before the correction. At this time, the contribution degree parameter P2 is set to P2=$|\Delta A10/S_{A10}|$+$|\Delta A12/S_{A10}|$. The contribution degree parameter P2 is a value proportional to the correction amount by the physician, and has a correlation with a magnitude of the error of the pre-learning discriminator 350. The parameter P2 is housed in the analysis result information DA1, and also housed in the concealed analysis result information DA2. The concealed analysis result information DA2 is housed in the learning data DCi and sent to the medical support server 300.

The calculation unit 306 of the medical support server 300 reads out the contribution degree parameter P2 from the learning data DCi and adds it to the contribution degree of the medical institution Mi. Thereby, the contribution degree parameter P2 having the correlation with the magnitude of the error of the pre-learning discriminator 350 can be reflected on the contribution degree of the medical institution Mi, so that the contribution degree of the learning data DCi can be appropriately evaluated.

(Method (B) of Calculating Contribution Degree)

Next, specific examples (example B-1 and example B-2) of the method (B) of calculating the contribution degree will be described.

Example B-1

In Example B-1, the data collecting and housing unit 302 houses a predetermined number (for example, 100) of medical images from among the second learning data used for creating the pre-learning discriminator 350 as a comparison data set. The comparison data set is created for each type of medical image (for example, an X-ray image or a CT image) and each examination part (for example, a chest or a head).

The calculation unit 306 compares the learning data (first learning data) DCi collected from the medical institution Mi with the comparison data set, and calculates the contribution degree parameter on the basis of the comparison result.

Specifically, the calculation unit 306 inputs the medical image included in the learning data DCi and the medical image included in the comparison data set to the learning unit 304. In this example, the learning unit 304 includes a convolutional neural network (CNN), performs image processing on each of the medical image included in the learning data DCi and the medical image included in the comparison data set, and performs normalization such as contrast or brightness. In addition, the learning unit 304 adjusts a magnitude of the examination part included in the medical image by enlarging or reducing the medical image included in the learning data DCi or the medical image included in the comparison data set as necessary.

Next, the learning unit 304 repeatedly performs convolution and pooling on each of the medical image included in the learning data DCi and the medical image included in the comparison data set to extract a feature vector. The calculation unit 306 acquires the feature vector from the learning unit 304, and calculates a contribution degree parameter P3 according to [equation 1]. The parameter P3 is a value that quantitatively indicates a magnitude of a feature difference between the medical image included in the learning data DCi and the medical image included in the comparison data set. The parameter P3 is housed in the analysis result information DA1, and also housed in the concealed analysis result information DA2. The concealed analysis result information DA2 is housed in the learning data DCi and sent to the medical support server 300.

The calculation unit 306 of the medical support server 300 reads out the contribution degree parameter P3 from the learning data DCi and adds it to the contribution degree of the medical institution Mi. Thereby, the contribution degree parameter P3 reflecting the magnitude of the feature difference between the medical image included in the learning data DCi and the medical image included in the comparison data set can be reflected in the contribution degree of the medical institution Mi, so that the contribution degree of the learning data DCi can be appropriately evaluated.

$$P3=|\vec{x_e}-\vec{x_t}| \quad \text{[Equation 1]}$$

$\vec{x_e}$: FEATURE VECTOR OF IMAGE IN THE COMPARISON DATA SET $\vec{x_t}$: FEATURE VECTOR OF IMAGE AFTER PROCESSING Example B-2

In example B-2, the contribution degree parameter is calculated on the basis of a comparison result between the first learning data and average data (average image) created from the second learning data.

In a case of acquiring the learning data (first learning data) DCi, the calculation unit 306 starts calculating the contribution degree. First, the calculation unit 306 is used for creating the pre-learning discriminator 350, and randomly extracts a predetermined number (for example, 100) of medical images from the second learning data housed in the data collecting and housing unit 302 to create the average image. Here, the average image is an image obtained by averaging pixel values of corresponding pixels between medical images. The corresponding pixels between the medical images are determined by performing positioning or enlargement or reduction of the medical images on the basis of, for example, the boundaries, centers, or centers of gravity of the organs included in the medical images. Here, the medical image used for creating the average image is the same as the learning data DCi and the type of the medical image (for example, an X-ray image or a CT image) and the examination part (for example, a chest or a head).

The calculation unit 306 compares the learning data (first learning data) DCi collected from the medical institution Mi with the average image, and calculates the contribution degree parameter on the basis of the comparison result.

Specifically, the calculation unit 306 inputs the medical image included in the learning data DCi and the average image to the learning unit 304. In this example, the learning unit 304 includes the convolutional neural network, performs image processing on each of the medical image included in the learning data DCi and the average image, and performs normalization such as contrast or brightness. In addition, the learning unit 304 adjusts a magnitude of the examination part included in the medical image by enlarging or reducing the medical image included in the learning data DCi or the medical image included in the average image as necessary.

Next, the learning unit 304 repeatedly performs convolution and pooling on each of the medical image included in the learning data DCi and the average image to extract a feature vector. The calculation unit 306 acquires the feature vector from the learning unit 304, and calculates a contribution degree parameter P4 according to [equation 2]. The parameter P4 is a value that quantitatively indicates a magnitude of a feature difference between the medical image included in the learning data DCi and the average image. The parameter P4 is housed in the analysis result information DA1, and also housed in the concealed analysis result information DA2. The concealed analysis result information DA2 is housed in the learning data DCi and sent to the medical support server 300.

The calculation unit 306 of the medical support server 300 reads out the contribution degree parameter P4 from the learning data DCi and adds it to the contribution degree of the medical institution Mi. Thereby, the contribution degree parameter P4 reflecting the magnitude of the feature difference between the medical image included in the learning data DCi and the medical image included in the comparison data set can be reflected in the contribution degree of the medical institution Mi, so that the contribution degree of the learning data DCi can be appropriately evaluated.

$$P4=|\vec{x_e}-\vec{x_t}| \quad \text{[Equation 2]}$$

$\vec{x_e}$: FEATURE VECTOR OF AVERAGE IMAGE $\vec{x_t}$: FEATURE VECTOR OF IMAGE AFTER PROCESSING The calculation formulas of the contribution degree parameters P1 to P4 are not limited to the above examples, and may be numerical values reflecting the correction amount by the physician or the magnitude of the error of the pre-learning discriminator 350.

(Method (C) of Calculating Contribution Degree)

Next, the method (C) of calculating the contribution degree will be described.

In the present example, the learning unit 304 of the medical support server 300 performs one-time learning that performs consultation of the learning data DCi from the medical institution Mi Then, the calculation unit 306 calculates the degree of accuracy improvement of the medical image identification engine before and after an update as a difference in a correct answer rate. Then, the calculation unit 306 calculates the contribution degree as a parameter proportional to the increase in the correct answer rate, for example, on the basis of the degree of the increase in the correct answer rate.

In the present embodiment, a medical image for an accuracy test may be input to a pre-learning discriminator 350 which is a medical image identification engine before the update and a learned discriminator 352 that is a medical image identification engine after the update, and the output may be compared with the correct answer data respectively to calculate the correct answer rate. In addition, before and after the update of the medical image identification engine, the correct answer rate may be calculated from a ratio of the number of medical images in which the diagnosis support information DA0 has been corrected by the physician of the medical institution Mi.

The methods (A) to (C) of calculating the contribution degree can be used alone or in combination of a plurality of methods. In a case where a plurality of methods are used in combination among the methods (A) to (C) of calculating the contribution degree, the total of the contribution degree parameter may be obtained by normalizing or weighted-adding the contribution degree parameter calculated by each method.

(Example of Data Processing Step)

Figure 12:
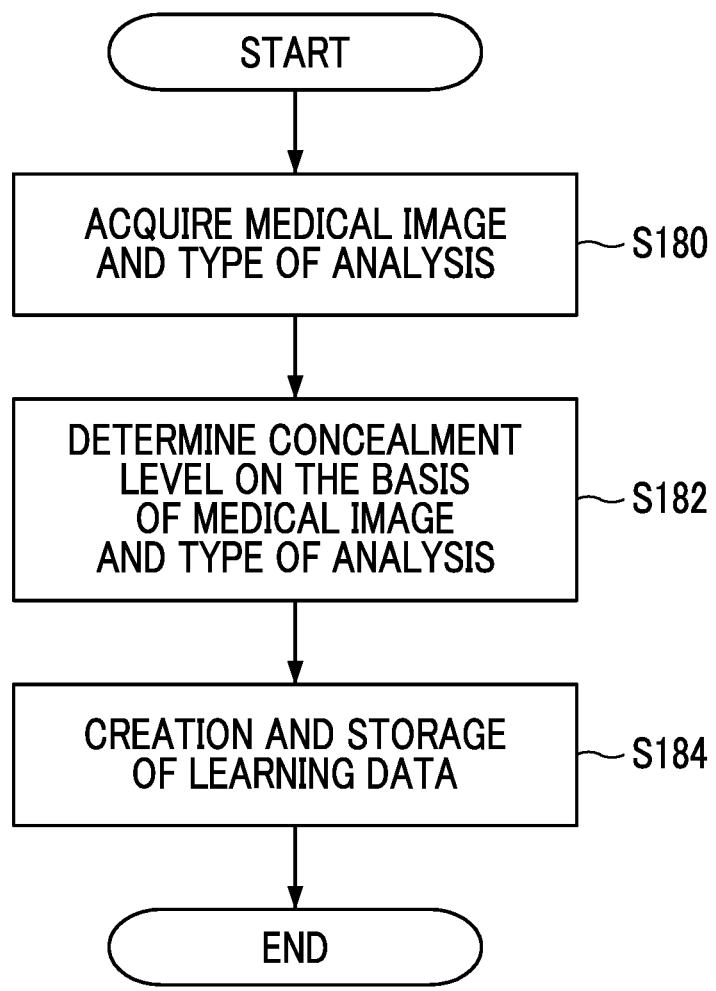
FIG. 12 is a flowchart illustrating a flow of processing in an example of setting concealment level in a data processing step in the medical image processing method.

Next, an example of data processing step according to the present embodiment will be described with reference to FIG. 12. FIG. 12 is a flowchart illustrating a flow of processing in an example of setting concealment level in a data processing step in the medical image processing method.

First, the data processing unit 118 acquires the medical image IMG1 included in the DICOM file F2, and acquires information on a type of the medical image IMG1 and information on a type of analysis (step S180). Here, the type of the medical image IMG1 includes, for example, information indicating an examination part (for example, a head, a chest, or the like) included in the medical image IMG1, information on a method of imaging the medical image IMG1, and information on a modality imaging the medical image IMG1 (for example, CT, MRI, or the like). The information on the type of analysis includes, for example, information on a lesion to be detected, information on a medical image identification engine used for detecting the lesion to be detected, and the like.

Next, the data processing unit 118 determines a concealment level on the basis of the medical image and the type of analysis (step S182). Then, the data processing unit 118 creates the learning data DC and stores it in the learning data storage unit 120 (step S184).

Table 4 shows an example of the concealment level, and Table 5 shows a correspondence relationship between the medical image identification engine and the concealment level.

In the example shown in Table 4, a type of patient identification information to be a target of the concealment processing increase in order from level I to level IV.

The data processing unit 118 determines the concealment level for each type of the medical image identification engine according to the concealment level shown in Table 5, and performs the concealment processing on the DICOM file F2. For example, in a case of detecting a brain disease, an image of the head is used. For this reason, level IV is applied, and body surface data is subject to concealment. Since the image of the head is not used in the detection of a fracture other than the head, the level II is applied.

TABLE 4

| Concealment Level | |
|---|---|
| Level I | Patient Name (Subject Name) |
| Level II | Patient Name (Subject Name), Age, Sex |
| Level III | Patient Name (Subject Name), Age, Sex, Disease |

TABLE 4-continued

| Concealment Level | |
|---|---|
| Level IV | Patient Name (Subject Name), Age, Sex, Disease, Body Surface Data |

TABLE 5

| Concealment Level for Each Type of Medical Image Identification Engine | |
|---|---|
| Detection of Cerebral Infarction, Stroke | Level IV |
| Measurement of Tumor | Level II |
| Detection of Fracture | Level II |
| Measurement of Cardio-Thoracic Ratio | Level I |

According to the example illustrated in FIG. 12, it is possible to perform appropriate concealment processing on the patient identification information by selecting a target of the concealment processing according to the type of the medical image and the type of analysis.

Second Embodiment

Figure 13:
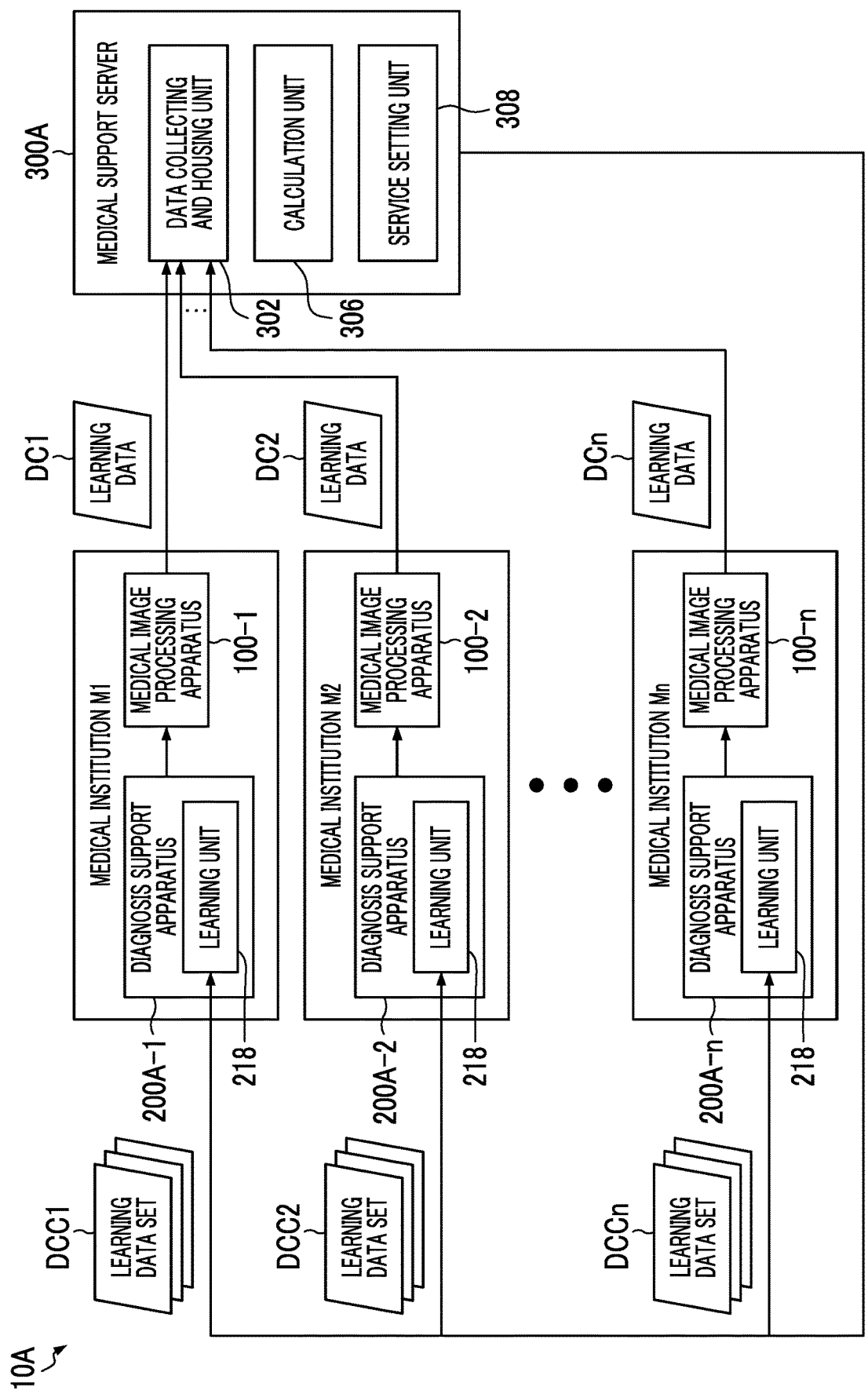
FIG. 13 is a block diagram illustrating a medical support system according to a second embodiment of the present invention.
Figure 14:
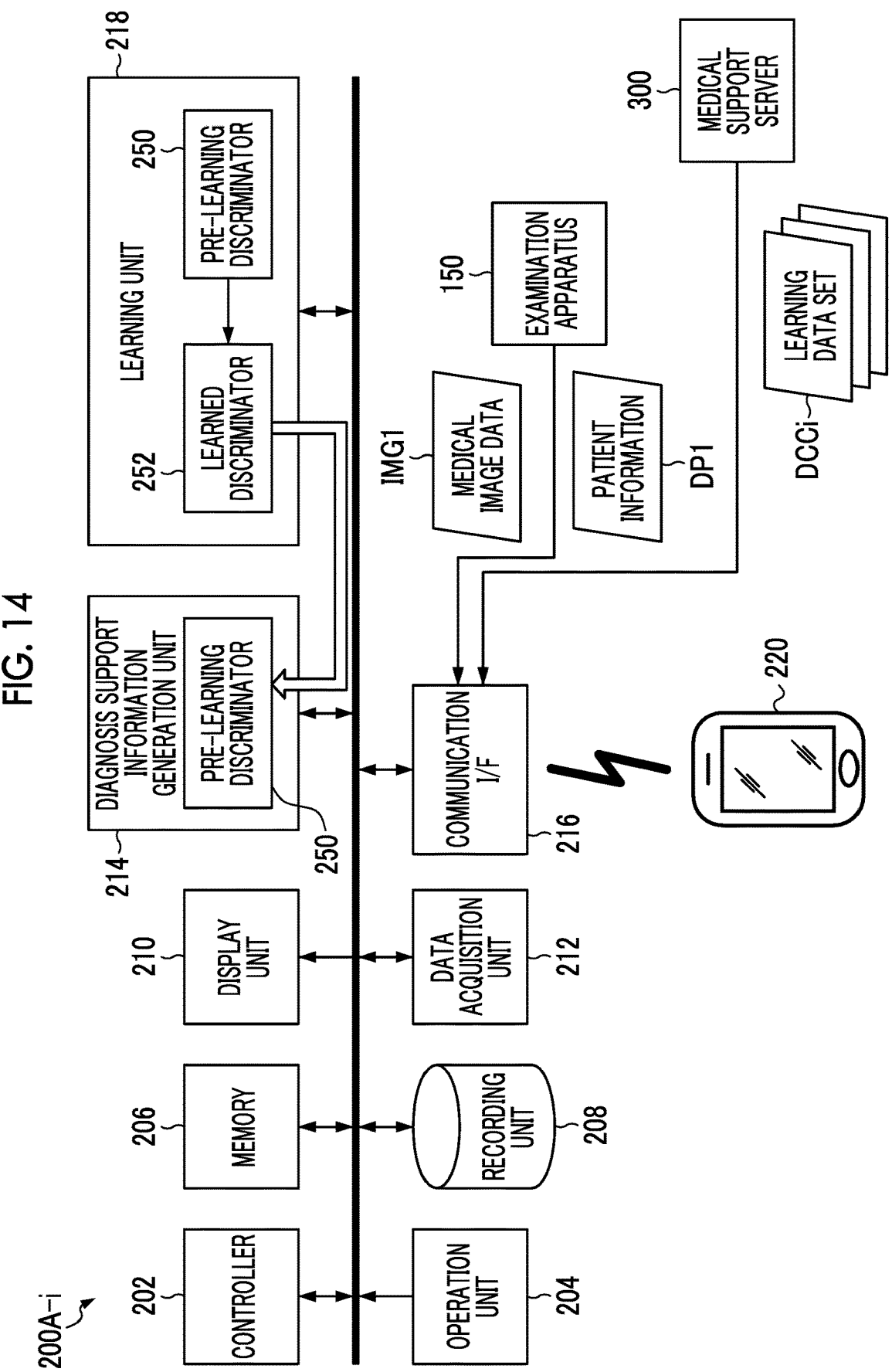
FIG. 14 is a block diagram illustrating a diagnosis support apparatus according to the second embodiment of the present invention.
Figure 15:
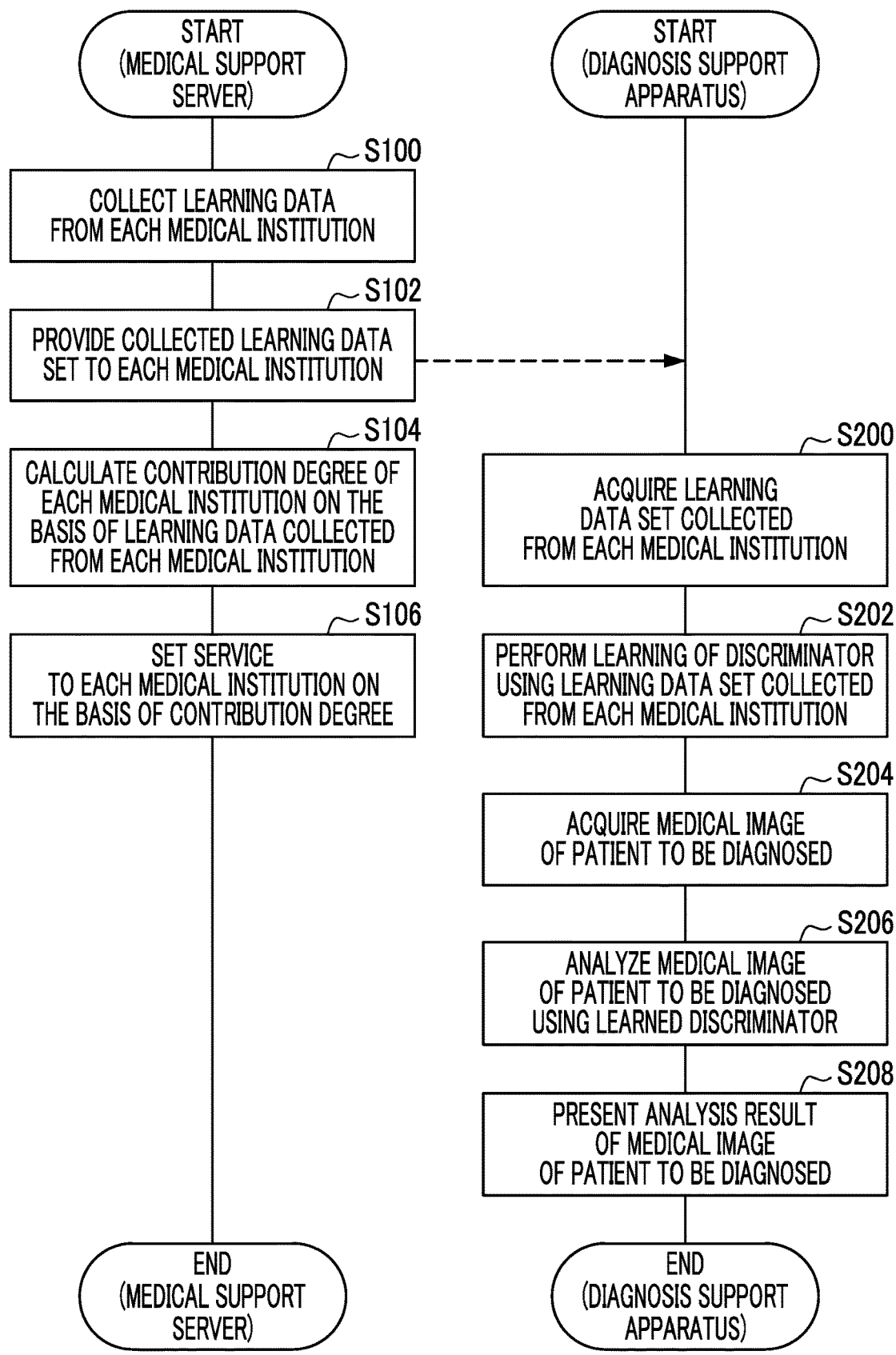
FIG. 15 is a flowchart illustrating a flow of processing in a diagnosis support method according to the second embodiment of the present invention.

Next, a second embodiment of the present invention will be described with reference to FIGS. 13 to 15. While the first embodiment is configured to perform learning of the medical image identification engine in the medical support server 300, the second embodiment is configured to perform learning of the medical image identification engine in the medical institution Mi side.

First, the medical support system according to the present embodiment will be described with reference to FIGS. 13 and 14. FIG. 13 is a block diagram illustrating a medical support system according to the second embodiment of the present invention. FIG. 14 is a block diagram illustrating a diagnosis support apparatus according to the second embodiment of the present invention.

In a medical support system 10A according to the present embodiment, a medical support server 300A collects the learning data DCi from the medical institution Mi. The learning data DCi is accumulated by the medical support server 300A to generate a set of learning data (a learning data set DCCi). The learning data set DCCi is transmitted from the medical support server 300A to each medical institution Mi.

The learning data set DCCi may include all the learning data DC1, DC2, . . . , DCn collected from the medical institutions M1, M2, . . . , Mn. The learning data set DCCi may be the learning data DC1, DC2, . . . , DCn excluding the learning data DCi of the medical institution Mi which is a transmission destination.

The calculation unit 306 in the present embodiment can calculate the contribution degree parameter using at least one of the methods (A) or (B) of calculating the contribution degree, for example.

The diagnosis support apparatus 200A-i according to the present embodiment further comprises a learning unit 218 in addition to the configuration described in the first embodiment.

The learning unit 218 causes a pre-learning discriminator 250 to perform learning using the learning data set DCCi acquired from the medical support server 300A, as in the first embodiment. In addition, in a case where it is the learning data DC1, DC2, . . . , DCn excluding the learning data DCi of the medical institution Mi which is the transmission destination, the learning data set DCCi performs learning using the learning data DCi in addition to the learning data set DCCi. Thereby, a learned discriminator 252 is generated. The diagnosis support information generation unit 214 updates the medical image identification engine by acquiring the learned discriminator 252 from the learning unit 218 and replacing it with the pre-learning discriminator 250.

Since the medical image processing apparatus and method according to the present embodiment are the same as those in the first embodiment, descriptions thereof will be omitted.

Next, the diagnosis support method (including a learning method) according to the present embodiment will be described with reference to FIG. 15. FIG. 15 is a flowchart illustrating a flow of processing in a diagnosis support method according to the second embodiment of the present invention.

First, in the medical support server 300A, the data collecting and housing unit 302 collects learning data DC1, DC2, . . . , DCn respectively from the medical institutions M1, M2, . . . , Mn (step S100). The learning data DC1, DC2, . . . , DCn collected from the medical institutions M1, M2, . . . , Mn are accumulated in the medical support server 300A to generate the learning data sets DCC1, DCC2, . . . , DCCn for each of the medical institutions M1, M2, . . . , Mn. The learning data sets DCC1, DCC2, . . . , DCCn are provided to the medical institutions M1, M2, . . . , Mn (step S102).

Next, the diagnosis support apparatus 200A-i acquires the learning data set DCCi from the medical support server 300A via the communication I/F 216 (step S200).

The learning unit 218 of the diagnosis support apparatus 200A-i causes the medical image identification engine (the pre-learning discriminator 250) to perform learning using the learning data set DCCi acquired from the medical support server 300A (step S202). The diagnosis support information generation unit 214 updates the medical image identification engine by replacing the learned discriminator 252 with the pre-learning discriminator 350.

Next, in a case where the data acquisition unit 212 of a diagnosis support apparatus 200A-i acquires a medical image of a patient to be diagnosed from the examination apparatus 150 (step S204), the diagnosis support information generation unit 214 analyzes the medical image of the patient to be diagnosed using the learned discriminator 352 (step S206). Then, the diagnosis support information generation unit 214 causes the display unit 210 to display the analysis result of the medical image of the patient to be diagnosed as the diagnosis support information DA0 (step S208).

In the medical support server 300A, the contribution degree of each medical institution Mi is calculated. First, the calculation unit 306 of the medical support server 300A calculates the contribution degree of each medical institution Mi on the basis of the learning data DCi collected from each medical institution Mi (step S104).

Next, the service setting unit 308 sets service to be provided to each medical institution Mi on the basis of the contribution degree of each medical institution Mi calculated in step S104 (step S106).

According to the present embodiment, similarly to the first embodiment, the medical institution Mi can be motivated to create learning data by setting the service according to the contribution degree. This makes it possible to continuously collect medical images from a plurality of medical institutions Mi and improve accuracy of the medical image identification engine.

In the second embodiment, the diagnosis support apparatus 200A-i of the medical institution Mi acquires the learning data DCi provided from the medical image processing apparatus 100-i of another medical institution via the medical support server 300A, but the present invention is not limited to thereto. For example, a peer to peer (P2P) type network may be formed by the medical image processing apparatus 100-i and the diagnosis support apparatus 200A-i of the medical institution Mi, and the diagnosis support apparatus 200A-i of the medical institution Mi may directly acquire the learning data DCi from the medical image processing apparatus 100-i of another medical institution.

In addition, in the first and second embodiments, although concealment processing is performed on the medical image IMG1 and the like, a configuration in which the concealment processing is not performed may be employed. In a case where the concealment processing is not performed, for example, the medical institution Mi and the medical support server 300 or 300A may be connected by a protected network such as a VPN or a dedicated line, or transmitting and receiving data between the medical institution Mi and the medical support server 300 or 300A may be encrypted.

Third Embodiment

Next, a third embodiment of the present invention will be described with reference to FIGS. 16 to 19. In the following description, the same configuration as those of the first embodiment are denoted by the same reference numeral, and description thereof is omitted.

In the first and second embodiments, the medical image identification engine is installed in the diagnosis support apparatus 200-i and 200A-i of the medical institution Mi to generate diagnosis support information. On the other hand, in the third embodiment, a service for generating the diagnosis support information using the medical image identification engine is provided as a service (for example, a web application service or a cloud application service) via a network from a medical support server 300B without installing the medical image identification engine in a diagnosis support apparatus 200B-i.

Figure 16:
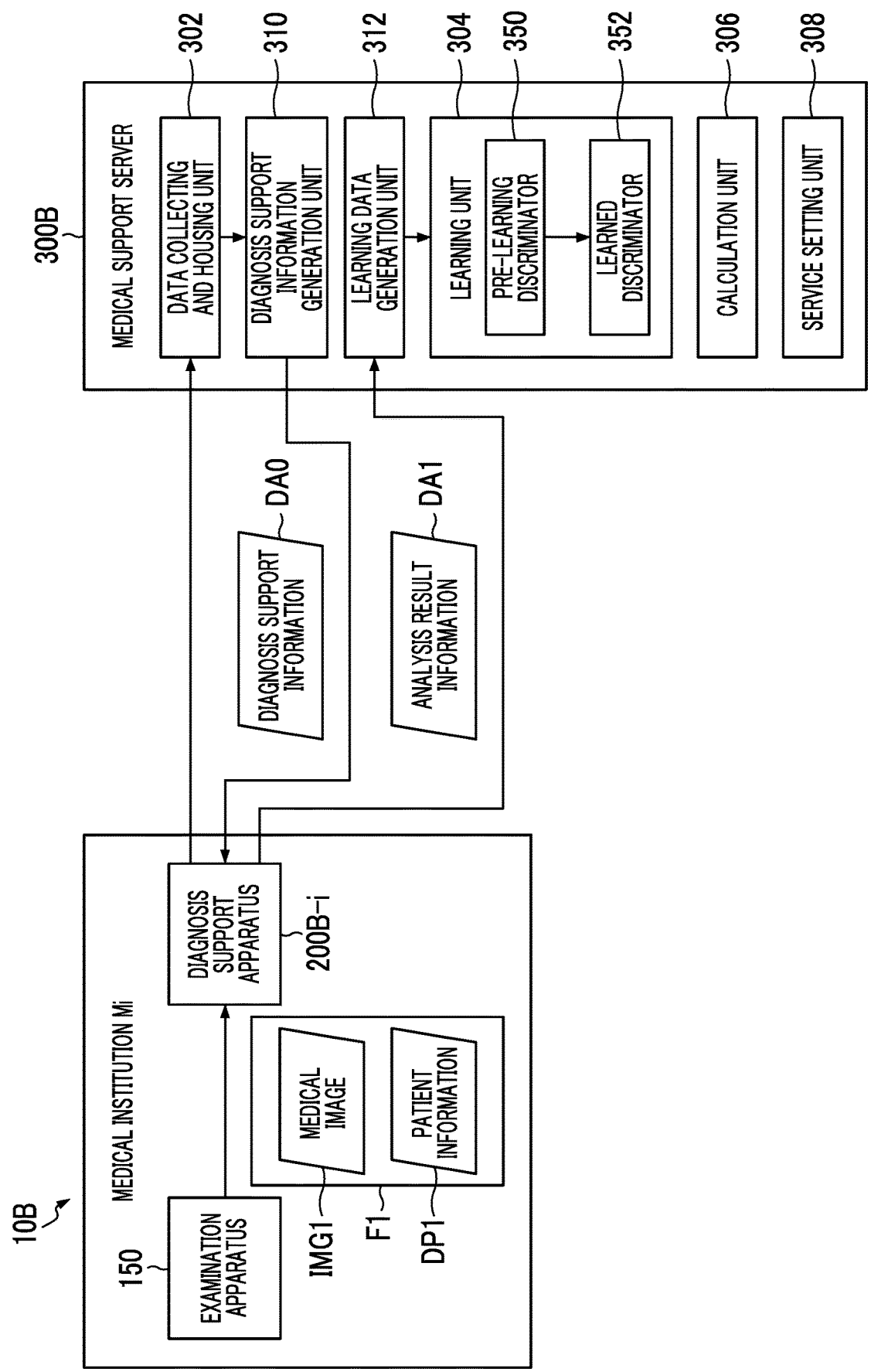
FIG. 16 is a block diagram for explaining a flow of processing in the medical support system according to a third embodiment of the present invention.
Figure 17:
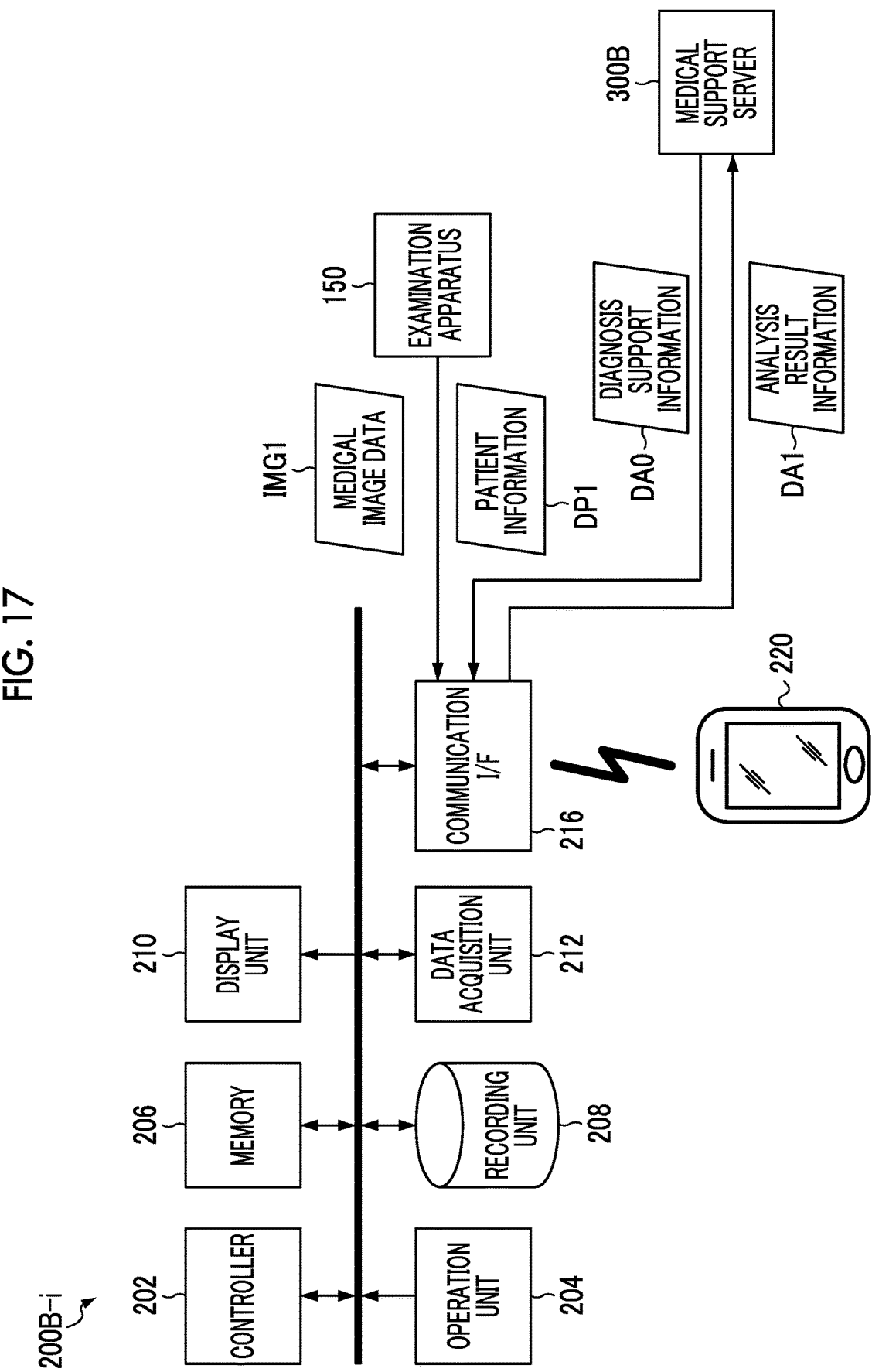
FIG. 17 is a block diagram illustrating a diagnosis support apparatus according to the third embodiment of the present invention.

FIG. 16 is a block diagram for explaining a flow of processing in the medical support system according to the third embodiment of the present invention, and FIG. 17 is a block diagram illustrating the diagnosis support apparatus according to the third embodiment of the present invention. In the present embodiment, the medical institution Mi and the medical support server 300B are connected by a protected network such as a VPN or a dedicated line. It is assumed that a confidentiality agreement is concluded between the medical institution Mi and a provider of a medical support service by the medical support server 300B with respect to patient identification information, and that a patient of the medical institution Mi has been given an appropriate informed consent with respect to the patient identification information.

The medical support server 300B according to the present embodiment comprises a diagnosis support information generation unit 310 and a learning data generation unit 312 in addition to the configuration of the first embodiment. On the other hand, the diagnosis support apparatus 200B-i according to the present embodiment has a configuration excluding the diagnosis support information generation unit 214.

The DICOM file F1 including the medical image IMG1 imaged by the examination apparatus 150 of the medical institution Mi is input to the diagnosis support apparatus 200B-i. In the present embodiment, in a case of receiving an instruction to generate the diagnosis support information from a physician via the operation unit 204 or the operation member of the physician terminal 220, the diagnosis support apparatus 200B-i transmits the DICOM file F1 to the medical support server 300B.

The data collecting and housing unit 302 acquires the DICOM file F1 and inputs it to the diagnosis support information generation unit 310.

The diagnosis support information generation unit 310 analyzes the medical image IMG1 included in the DICOM file F1 using the medical image identification engine (the pre-learning discriminator 350), and generates the diagnosis support information DA0.

The diagnosis support information DA0 is transmitted from the diagnosis support information generation unit 310 to the diagnosis support apparatus 200B-i, and is displayed on the display unit 210 of the diagnosis support apparatus 200B-i or the display screen of the physician terminal 220 together with the medical image IMG1.

The physician observes the medical image IMG1 and the diagnosis support information DA0, and inputs approval or correction of the diagnosis support information DA0 using the operation unit 204 or an operation member of the physician terminal 220. In a case where the approval is input to the diagnosis support information DA0, the controller 202 generates analysis result information (correct answer data) DA1 by adding additional information indicating that it has been approved by the physician to the diagnosis support information DA0. On the other hand, in a case where the correction is input to the diagnosis support information DA0, the controller 202 generates the analysis result information (correct answer data) DA1 by adding additional information indicating that it has been corrected by the physician and the content of the correction to the diagnosis support information DA0. This analysis result information DA1 is transmitted to the learning data generation unit 312 of the medical support server 300B via the communication I/F 216 of the diagnosis support apparatus 200B-i.

Figure 18:
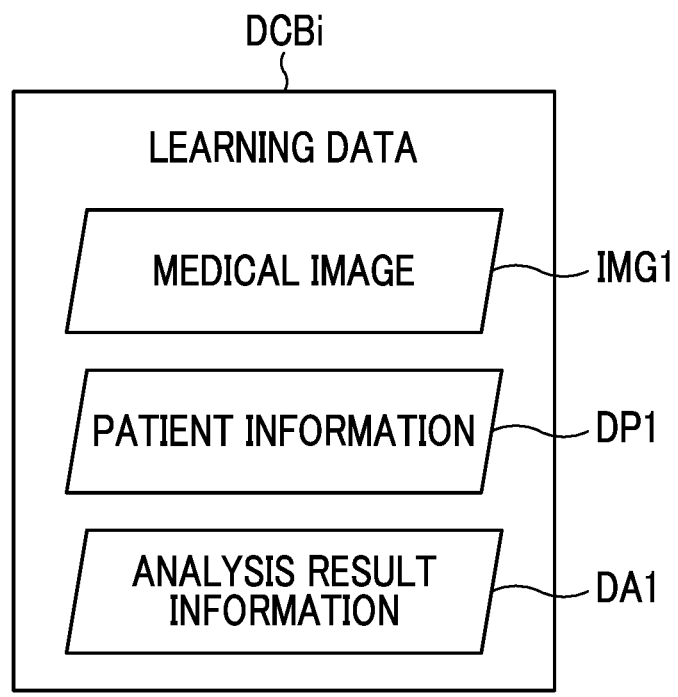
FIG. 18 is a data block diagram illustrating learning data according to the third embodiment of the present invention.

The learning data generation unit 312 generates learning data DCBi by adding the analysis result information DA1 to the DICOM file F1 collected from the medical institution Mi. As illustrated in FIG. 18, the learning data DCBi includes the analysis result information DA1 in addition to the medical image IMG1 and the patient information DPi included in the DICOM file F1.

The learning unit 304 causes the medical image identification engine (the pre-learning discriminator 350) to perform learning using the learning data DCBi.

The calculation unit 306 calculates the contribution degree by, for example, at least one of the methods (A) or (B) of calculating the contribution degree using the learning data DCBi. In the present embodiment, it is also possible to use the method (C) of calculating the contribution degree.

Figure 19:
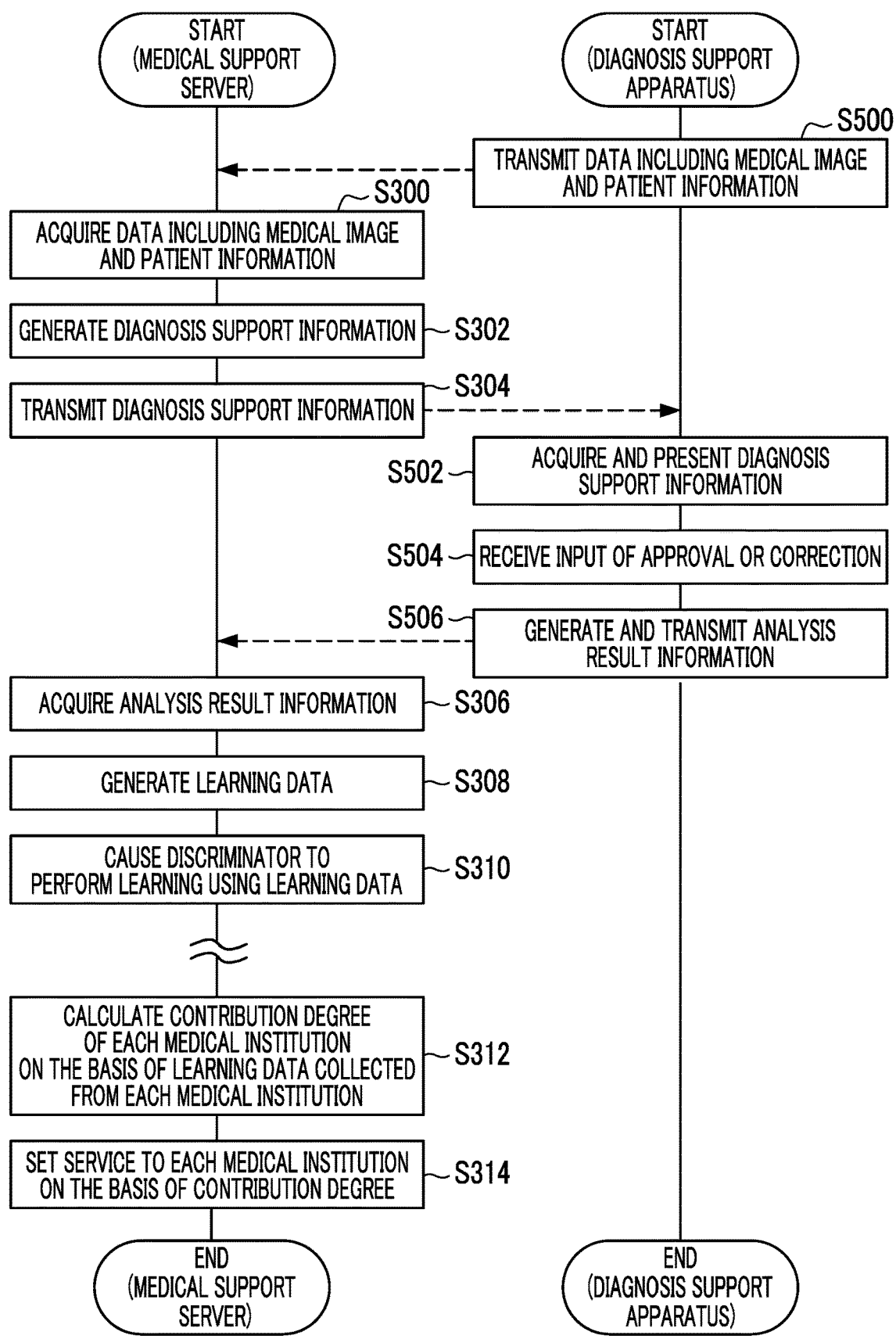
FIG. 19 is a flowchart illustrating a flow of processing in a diagnosis support method according to the third embodiment of the present invention.

Hereinafter, the diagnosis support method (including a learning method) according to the third embodiment of the present invention will be described with reference to FIG. 19. FIG. 19 is a flowchart illustrating a flow of processing in a diagnosis support method according to the third embodiment of the present invention.

First, in the diagnosis support apparatus 200B-i, in a case where an input of a generation instruction of the diagnosis support information DA0 is received, the DICOM file F1 including the medical image IMG1 and the patient information DPi is transmitted from the diagnosis support apparatus 200B-i to the medical support server 300B (step S500).

The data collecting and housing unit 302 of the medical support server 300B acquires the DICOM file F1 and inputs it to the diagnosis support information generation unit 310 (step S300).

The diagnosis support information generation unit 310 analyzes the medical image IMG1 and the like by the pre-learning discriminator 350, generates diagnosis support information DA0 (step S302) and transmits it to the diagnosis support apparatus 200B-i (step S304).

The controller 202 of the diagnosis support apparatus 200B-i displays the diagnosis support information DA0 on the display unit 210 or the display screen of the physician terminal 220 together with the medical image IMG1 (step S502).

In a case of receiving an input of approval or correction from the physician for the diagnosis support information DA0 via the operation unit 204 of the diagnosis support apparatus 200B-i or the operation member of the physician terminal 220 (step S504), the controller 202 generates the analysis result information DA1 and transmits it to the medical support server 300B (step S506).

In a case of acquiring the analysis result information DA1 (step S306), the learning data generation unit 312 of the medical support server 300B adds the analysis result information DA1 to the DICOM file F1 to generate the learning data DCBi (step S308).

The learning unit 304 causes the pre-learning discriminator 350 to perform learning using the learning data DCBi (step S310). Thereby, the medical image identification engine is updated in the medical support server 300B.

Next, in the medical support server 300B, the contribution degree of each medical institution Mi is calculated and the service settings are set. Steps S312 and S314 may be performed periodically, or may be executed according to the number of accumulated learning data DCi. In a case where the method (C) of calculating the contribution degree is used, the steps S312 and S314 may be executed after the pre-learning discriminator 350 has learned and after the learned discriminator 352 has generated the diagnosis support information DA0 a sufficient number of times for calculating the accuracy.

First, the calculation unit 306 of the medical support server 300B calculates the contribution degree of each medical institution Mi on the basis of the learning data DCi collected from each medical institution Mi (step S312).

Next, the service setting unit 308 sets service to be provided to each medical institution Mi on the basis of the contribution degree of each medical institution Mi calculated in step S312 (step S314).

In the present embodiment, in addition to the service content described in the first embodiment, for example, the service setting unit 308 may set allocation of a resource in a case where the diagnosis support apparatus 200B-i of the medical institution Mi uses the medical support server 300B on the basis of the contribution degree. Here, the "resource" refers to hardware or a hardware environment that can be used by a program in a case where the computer executes the program using a calculation apparatus. In addition, in a case of generating the diagnosis support information DA0 on the basis of an instruction from the diagnosis support apparatus 200B-i, the resource may be a utilization rate of the calculation apparatus (the diagnosis support information generation unit 310 or the like) in the medical support server 300B, a storage capacity, a memory capacity, a network band, or the number of accesses that can be simultaneously accessed from (the diagnosis support apparatus 200B-i of) the medical institution Mi. In the present embodiment, the service setting unit 308 can allocate more resources to the medical institution Mi having a higher contribution degree.

According to the present embodiment, similarly to the first and second embodiments, the medical institution Mi can be motivated to create learning data by setting the service according to the contribution degree. This makes it possible to continuously collect medical images from a plurality of medical institutions Mi and improve accuracy of the medical image identification engine.

In the present embodiment, in a case where the medical image processing apparatus 100-i is provided in the medical institution Mi and transmits a medical image and patient information, the concealment processing of the patient identification information may be performed.

ABOUT THE INVENTION OF THE PROGRAM

The present invention can also be realized as a program (a learning program) for causing a computer to realize the above processing (a learning method), or a non-transitory recording medium or a program product housing such a program. By applying such a program to a computer, it becomes possible for arithmetic unit, a recording unit, and the like of the computer to realize a function corresponding to each step of the learning method according to the present embodiment.

In each of the embodiments, for example, in the medical image processing apparatus 100-i, the diagnosis support apparatus 200-i, 200A-i, and 200B-i, and the medical support servers 300, 300A, and 300B a hardware structure of a processing unit that executes various types of processing can be realized as the following various types of processors. The various processors include a central processing unit (CPU) as a general-purpose processor functioning as various processing units by executing software (program), a programmable logic device (PLD) as a processor of which the circuit configuration can be changed after manufacturing such as a field programmable gate array (FPGA), and a dedicated electric circuit which is a processor having a circuit configuration specifically designed to execute specific processing such as an application specific integrated circuit (ASIC).

One processing unit may be configured with one of these various processors, or may be configured with two or more same kind or different kinds of processors (for example, a plurality of FPGAs, or a combination of a CPU and an FPGA). Further, a plurality of processing units may be formed of one processor. As an example where a plurality of processing units is configured with one processor, first, there is an aspect where one processor is configured with a combination of one or more CPUs and software as typified by a computer, such as a client or a server, and functions as a plurality of processing units. Second, as represented by a system on chip (SoC), there is an aspect in which a processor that realizes the functions of the entire system including the plurality of processing units by one integrated circuit (IC) chip is used. In this way, various processing units are formed using one or more of the above-mentioned various processors as hardware structures.

In addition, the hardware structures of these various processors are more specifically electrical circuitry where circuit elements such as semiconductor elements, are combined.

EXPLANATION OF REFERENCES 10, 10A: medical support system
M1, M2, . . . , Mn: medical institutions
100-1, 100-2, . . . , 100-n: medical image processing apparatus
102: controller
104: operation unit
106: memory
108: recording unit
110: display unit
112: medical image reception unit
114: analysis result acquisition unit
116: detection unit
118: data processing unit
120: learning data storage unit
122: communication I/F
200-1, 200-2, . . . , 200-n, 200A-1, 200A-2, . . . , 200A-n, 200B-i: diagnosis support apparatus
202: controller
204: operation unit
206: memory
208: recording unit
210: display unit
212: data acquisition unit
214: diagnosis support information generation unit
216: communication I/F
218: learning unit
220: physician terminal
250: pre-learning discriminator
252: learned discriminator
300, 300A, 300B: medical support server
302: data collecting and housing unit
304: learning unit
306: calculation unit
308: service setting unit
310: diagnosis support information generation unit
312: learning data generation unit
350: pre-learning discriminator
352: learned discriminator
DP1: patient information
DP2: concealed patient information
DA0: diagnosis support information
DA1: analysis result information
DA2: concealed analysis result information
DC1, DC2, . . . , DCn, DCBi: learning data
DCC1, DCC2, . . . , DCCn: learning data set
F1, F2: DICOM file
IMG1: medical image
IMG2: concealed medical image
S10 to S14: each step of medical image processing method
S30 to S38, S50 to S54, S100 to S106, S200 to S208, S300 to S314, S500 to S506: each step of diagnosis support method
S180 to S184: each step of creating and storing learning data

What is claimed is:

1. A learning system comprising:
a processor configured to
receive an input of first learning data from a user, the first learning data comprising an image and analysis result information of the image;
calculate a contribution degree of the first learning data to learning of a discriminator for each user,
wherein the discriminator is an image identification engine that is created by second learning data, the second learning data comprising another image and analysis result information of the another image,
wherein the contribution degree is calculated on the basis of at least one of a comparison result between the first learning data and the second learning data or a comparison result between an output obtained by inputting the first learning data to the discriminator and correct answer data corresponding to the first learning data; and set a service for the user on the basis of the contribution degree calculated for each user, wherein when the processor calculates the contribution degree on the basis of the comparison result between the first learning data and the second learning data, the processor calculates the contribution degree on the basis of a difference between a comparison data set including the second learning data and the first learning data, and on the basis of a difference between a feature vector obtained from an image included in the second learning data and a feature vector obtained from an image included in the first learning data.

2. The learning system according to claim 1, wherein the processor is further configured to receive an input of the correct answer data for an output obtained by inputting the first learning data to the discriminator, and wherein the processor calculates the contribution degree on the basis of a result of comparing the output with the correct answer data.

3. The learning system according to claim 2, wherein the processor receives an input of correction of at least one of a contour or a size of a region extracted from an image included in the first learning data by the discriminator, and wherein the processor calculates the contribution degree on the basis of an amount of the correction.

4. The learning system according to claim 1, wherein the processor calculates a difference in accuracy of an image analysis result in the discriminator before and after learning using the first learning data, and calculates the contribution degree of the first learning data to learning of the discriminator for each user on the basis of the difference in accuracy.

5. The learning system according to claim 1, wherein the processor receives an input of data including a medical image of a patient as the first learning data, and wherein the processor is further configured to create and store data in which identification information capable of identifying the patient is concealed, in the first learning data.

6. A learning method performed in a learning system comprising:

receiving an input of first learning data from a user, the first learning data comprising an image and analysis result information of the image;

calculating a contribution degree of the first learning data to learning of a discriminator for each user, wherein the discriminator is an image identification engine that is created by second learning data, the second learning data comprising another image and analysis result information of the another image, wherein the contribution degree is calculated on the basis of at least one of a comparison result between the first learning data and the second learning data or a comparison result between an output obtained by inputting the first learning data to the discriminator and correct answer data corresponding to the first learning data; and setting a service for the user on the basis of the contribution degree calculated for each user, wherein when the contribution degree is calculated on the basis of the comparison result between the first learning data and the second learning data, the contribution degree is calculated on the basis of a difference between a comparison data set including the second learning data and the first learning data, and on the basis of a difference between a feature vector obtained from an image included in the second learning data and a feature vector obtained from an image included in the first learning data.

7. A non-transitory, computer-readable recording medium which records therein, computer instructions that, when executed by a computer, causes the computer to realize:

a function of receiving an input of first learning data from a user, the first learning data comprising an image and analysis result information of the image;

a function of calculating a contribution degree of the first learning data to learning of a discriminator for each user, wherein the discriminator is an image identification engine that is created by second learning data, the second learning data comprising another image and analysis result information of the another image, wherein the contribution degree is calculated on the basis of at least one of a comparison result between the first learning data and the second learning data or a comparison result between an output obtained by inputting the first learning data to the discriminator and correct answer data corresponding to the first learning data; and a function of setting a service for the user on the basis of the contribution degree calculated for each user, wherein when the contribution degree is calculated on the basis of the comparison result between the first learning data and the second learning data, the contribution degree is calculated on the basis of a difference between a comparison data set including the second learning data and the first learning data, and on the basis of a difference between a feature vector obtained from an image included in the second learning data and a feature vector obtained from an image included in the first learning data.

8. A learning system comprising:

a processor configured to receive an input of first learning data from a user, the first learning data comprising an image and analysis result information of the image;

calculate a contribution degree of the first learning data to learning of a discriminator for each user, wherein the discriminator is an image identification engine that is created by second learning data, the second learning data comprising another image and analysis result information of the another image, wherein the contribution degree is calculated on the basis of at least one of a comparison result between the first learning data and the second learning data or a comparison result between an output obtained by inputting the first learning data to the discriminator and correct answer data corresponding to the first learning data; and set a service for the user on the basis of the contribution degree calculated for each user, wherein when the processor calculates the contribution degree on the basis of the comparison result between the first learning data and the second learning data, the processor calculates the contribution degree on the basis of a difference between average data created from the second learning data used for creating the discriminator and the first learning data.

9. A learning system comprising:

a processor configured to receive an input of first learning data from a user, the first learning data comprising an image and analysis result information of the image;

calculate a contribution degree of the first learning data to learning of a discriminator for each user, wherein the discriminator is an image identification engine that is created by second learning data, the second learning data comprising another image and analysis result information of the another image, wherein the contribution degree is calculated on the basis of at least one of a comparison result between the first learning data and the second learning data or a comparison result between an output obtained by inputting the first learning data to the discriminator and correct answer data corresponding to the first learning data; and set a service for the user on the basis of the contribution degree calculated for each user, wherein when the processor calculates the contribution degree on the basis of the comparison result between the first learning data and the second learning data, the processor calculates the contribution degree on the basis of a difference between average data created from the second learning data used for creating the discriminator and the first learning data, and on the basis of a difference between a feature vector obtained from an average image created from an image included in the second learning data and a feature vector obtained from an image included in the first learning data.

* * * * *